(12) United States Patent
Kudithipudi et al.

(10) Patent No.: US 11,981,903 B2
(45) Date of Patent: *May 14, 2024

(54) TOBACCO HAVING ALTERED LEAF PROPERTIES AND METHODS OF MAKING AND USING

(71) Applicant: Altria Client Services LLC, Richmond, VA (US)

(72) Inventors: Chengalrayan Kudithipudi, Midlothian, VA (US); Alec J. Hayes, Chesterfield, VA (US)

(73) Assignee: Altria Client Services LLC, Richmond, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/936,001

(22) Filed: Sep. 28, 2022

(65) Prior Publication Data

US 2023/0122459 A1 Apr. 20, 2023

Related U.S. Application Data

(63) Continuation of application No. 17/096,213, filed on Nov. 12, 2020, now Pat. No. 11,492,633, which is a continuation of application No. 16/149,456, filed on Oct. 2, 2018, now Pat. No. 10,851,384, which is a continuation of application No. 14/789,177, filed on Jul. 1, 2015, now Pat. No. 10,113,174.

(60) Provisional application No. 62/019,936, filed on Jul. 2, 2014.

(51) Int. Cl.
*C12N 15/82* (2006.01)
*A01H 1/06* (2006.01)
*A24B 13/00* (2006.01)

(52) U.S. Cl.
CPC .......... *C12N 15/8243* (2013.01); *A01H 1/06* (2013.01); *A24B 13/00* (2013.01); *C12N 15/8218* (2013.01)

(58) Field of Classification Search
None
See application file for complete search history.

(56) References Cited

U.S. PATENT DOCUMENTS

| | | |
|---|---|---|
| 3,500,834 A | 3/1970 | Taylor et al. |
| 4,516,590 A | 5/1985 | Teng |
| 4,528,993 A | 7/1985 | Sensabaugh, Jr. et al. |
| 4,660,577 A | 4/1987 | Sensabaugh et al. |
| 4,683,195 A | 7/1987 | Mullis et al. |
| 4,683,202 A | 7/1987 | Mullis |
| 4,761,373 A | 8/1988 | Anderson et al. |
| 4,769,061 A | 9/1988 | Comai |
| 4,800,159 A | 1/1989 | Mullis et al. |
| 4,810,648 A | 3/1989 | Stalker |
| 4,848,373 A | 7/1989 | Lenkey |
| 4,940,835 A | 7/1990 | Shah et al. |
| 4,965,188 A | 10/1990 | Mullis et al. |
| 4,975,374 A | 12/1990 | Goodman et al. |
| 5,013,659 A | 5/1991 | Bedbrook et al. |
| 5,162,602 A | 11/1992 | Somers et al. |
| 5,164,180 A | 11/1992 | Payne et al. |
| 5,276,268 A | 1/1994 | Strauch et al. |
| 5,372,149 A | 12/1994 | Roth et al. |
| 5,545,565 A | 8/1996 | De Greve et al. |
| 5,561,236 A | 10/1996 | Leemans et al. |
| 5,767,366 A | 6/1998 | Sathasivan et al. |
| 5,879,903 A | 3/1999 | Strauch et al. |
| 5,928,937 A | 7/1999 | Kakefuda et al. |
| 6,084,155 A | 7/2000 | Volrath et al. |
| 6,166,302 A | 12/2000 | Merlo et al. |
| 6,451,732 B1 | 9/2002 | Beckett et al. |
| 6,451,735 B1 | 9/2002 | Ottaway et al. |
| 7,884,263 B2 | 2/2011 | Dewey et al. |
| 2001/0016956 A1 | 8/2001 | Ward et al. |
| 2004/0118422 A1 | 6/2004 | Lundin et al. |
| 2005/0178398 A1 | 8/2005 | Breslin et al. |
| 2005/0244521 A1 | 11/2005 | Strickland et al. |
| 2006/0191548 A1 | 8/2006 | Strickland et al. |
| 2012/0024301 A1 | 2/2012 | Carroll et al. |
| 2012/0031414 A1 | 2/2012 | Atchley et al. |
| 2012/0031416 A1 | 2/2012 | Atchley et al. |
| 2015/0245585 A1 | 9/2015 | Lewis et al. |

FOREIGN PATENT DOCUMENTS

EP 0242246 11/1992

OTHER PUBLICATIONS

Wang, Jianmin, et al. "Characterization of cDNAs differentially expressed in roots of tobacco (*Nicotiana tabacum* cv Burley 21) during the early stages of alkaloid biosynthesis." Plant Science 158.1-2 (2000): 19-32. (Year: 2000).*
Chen et al., "TALENs: Customizable molecular DNA scissors for genome engineering in plants," *Journal of Genetics and Genomics*, 40(6):271-279.
Chenna et al., "Multiple sequence alignment with the Clustal series of programs," *Nucleic Acids Research*, 31(13):3497-3500 (2003).
Fischoff et al., "Insect Tolerant Transgenic Tomato Plants," *Nature Biotechnology*, 5:807-813 (1987).
GenBank DNA sequence entry EB678479.1, Apr. 27, 2006, www.ncbi.nlm.nih.gov/nucest/EB678479.1.
Heggestad et al., "Development of Burley 21, the first wildfire-resistant tobacco variety, including result of variety trials," University of Tennessee Agricultural Experiment Station, Bulletin 321 (1960).
Hibi et al., "Gene Expression in Tobacco 5-32 Low-Nicotine Mutants," *Plant Cell*, 6:723-735 (1994).
International Preliminary Report on Patentability in International Application No. PCT/US2015/038813, dated Jul. 10, 2016, 9 pages.
International Search Report and Written Opinion in International Application No. PCT/US2014/028242, dated Oct. 9, 2015, 14 pages.

(Continued)

*Primary Examiner* — Weihua Fan
(74) *Attorney, Agent, or Firm* — Arnold & Porter Kaye Scholer LLP

(57) ABSTRACT

This disclosure provides tobacco plants having a mutation in PR50 and transgenic tobacco plants containing a PR50 RNAi, and methods of making and using such plants.

20 Claims, 4 Drawing Sheets

Specification includes a Sequence Listing.

(56) References Cited

OTHER PUBLICATIONS

Legacy Tobacco Document Library (Bates Document #523267826/7833, Jul. 1, 1988, Memorandum on the Proposed Burley Tobacco Grade Index).
Legg et al., "Registration of LA Burley 21 Tobacco Germplasm," *Crop Science*, 10:212 (1970).
Li et al., "Modularly assembled designer TAL effector nucleases for targeted gene knockout and gene replacement in eukaiyotes," *Nucleic Acids Research*, 39(14):6315-6325 (2011).
Miller et al., "A Grade Index for Type 22 and 23 Fire-cured tobacco," *Tobacco International*, 192:55-57 (1990).
Nielsen et al., "Registration of HI and LI burley 21 tobacco germplasms," *Crop Science*, 28:206 (1988).
Official Standard Grade published by the Agricultural Marketing Service of the US Department of Agriculture (7 U.S.C. §511).
Quiapim et al., "Analysis of the Nicotiana tabacum stigma/style transcriptome reveals gene expression differences between wet and dry stigma species," *Plant Physiology*, 149(3):1211-1230 (2009).
Smith et al., "Total silencing by intron-spliced hairpin RNAs," *Nature*, 407:319-320 (2000).
Vaeck et al., "Transgenic plants protected from insect attack," *Nature*, 328:33-37 (1997).
Wang et al., "Silencing of PMT expression caused a surge of anatabine accumulation in tobacco," *Molecular Biology Reports*, 36(8):2285-2289 (2009).
Wang et al., "Characterization of cDNAs differentially expressed in roots of tobacco (*Nicotiana tabacum* cv Burley 21) during the early stages of alkaloid biosynthesis," *Plant Science*, 158(1-2):19-32 (2000).
Waterhouse et al., "Exploring plant 8-32 genomes by RNA-induced gene silencing," *Nature Reviews: Genetics*, 4:29-38 (2003).
Wesley et al., "Construct design for efficient, effective and high-throughput gene silencing in plants," *The Plant Journal*, 27(6):581-590 (2001).
Wright et al., "High-frequency homologous recombination in plants mediated by zinc-finger nulceases," *The Plant Journal*, 44:693-705 (2005).
Yoo et al., "*Arabidopsis* mesophyll protoplasts: a versatile cell system for transient gene expression alalysis," *Nature Protocols*, 2(7):1565-1572 (2007).
Dayhoff et al., "22: A Model of Evolutionary Change in Proteins," Atlas of Protein Sequence and Structure, 5(3), pp. 345-352, (1978), available online: https://chagall.med.cornell.edu/BioinfoCourse/PDFs/Lecture2/Dayhoff1978.pdf.
"Draft for Diplomatic Conference for the Revision of the International Convention for the Protection of New Varieties of Plants," (of Dec. 2, 1961, as revised at Geneva on Nov. 10, 1972; on Oct. 23, 1978; and on Mar. 19, 1991),54 pages, Mar. 4-19, 1991 (Geneva, Switzerland).

\* cited by examiner

|  |  | 20 | | 40 | | 60 |  |
|---|---|---|---|---|---|---|---|
| SEQ ID NO: 2 | ATGTCAGGAG | AGGATGCTGC | TGTTCCTGTT | GT----TGCTG | CCGAGACTCC | TGCTCCAGCA | 57 |
| SEQ ID NO: 23 | ATGTCAGGAG | AGGATGCTGC | TGTTCCTGTT | GTCGCTGCTG | CCGAGACTCC | TGCTCCAGCA | 60 |
| SEQ ID NO: 11 | ATGTCGGGAG | AGGATGTTGC | TGTTGCTGTT | ---------G | CCGAGGCTCC | TGCTCCATCA | 51 |
| SEQ ID NO: 12 | ATGTCTGGAG | AGGATGCTGC | TGTTGCTGTT | CCC----GCTG | TTGAGACTCC | TTCTCCAGCA | 57 |
| SEQ ID NO: 13 | ATGTCAGGAG | AGGATGTTGC | TGTTGCTGTT | ---------G | CCGAGGCTCC | TGCTCCAGCA | 51 |
| SEQ ID NO: 14 | ATGTCTGGAG | AGGATGCTGC | TGTTGCTGTT | CCC----GCTG | TCGAGACTCC | TGCTCCAGCA | 57 |
|  |  | 80 | | 100 | | 120 |  |
| SEQ ID NO: 2 | CTTGGGGAGC | CCATGGACAT | CATGACCGCT | CTGCAGCTGG | TGCTCAGGAA | GTCTAAAGCT | 117 |
| SEQ ID NO: 23 | CTTGGGGAGC | CCATGGACAT | CATGACCGCA | CTACAGCTGG | TGCTAAAGAA | GTCTAAAGCT | 120 |
| SEQ ID NO: 11 | CTTGGAGAGC | CCATGGACAT | CATGACTGCT | TTGCAGCTGG | TGCTGAGGAA | GTCTAAGGCT | 111 |
| SEQ ID NO: 12 | CTTGGAGAGC | CCATGGATAT | CATGACTGCT | CTACAGCTGG | TGCTCAGGAA | GTCTAAAGCT | 117 |
| SEQ ID NO: 13 | CTTGGAGAGC | CCATGGACAT | CATGACTGCT | TTGCAGCTGG | TGCTGAGGAA | GTCTAGAGCT | 111 |
| SEQ ID NO: 14 | CTTGGAGAGC | CCATGGATAT | CATGACTGCT | CTGCAGCTGG | TGCTCAGGAA | GTCTAAAGCT | 117 |
|  |  | 140 | | 160 | | 180 |  |
| SEQ ID NO: 2 | CATGGAGGAC | TTGCTCGAGG | ACTCCATGAA | GGTGCTAAGG | TGATTGAGAA | GCATGCTGCG | 177 |
| SEQ ID NO: 23 | CATGGAGGAC | TTGCTCGAGG | ACTCCATGAA | GGTGCTAAGG | TGATTGAGAA | GCATGCTGCA | 180 |
| SEQ ID NO: 11 | CATGGAGGCC | TCTCTCGGGG | ACTACATGAA | GGTGCAAAGG | TGATTGAGAA | GCATGCTGCA | 171 |
| SEQ ID NO: 12 | CATGGAGGGC | TTGCTCGAGG | ACTTCATGAA | GGTGCTAAGG | TCATTGAGAA | GCATGCTGCA | 177 |
| SEQ ID NO: 13 | CATGGAGGCC | TCTCTCGGGG | ACTACATGAA | GGTGCAAAGG | TGATTGAGAA | GCATGCTGCA | 171 |
| SEQ ID NO: 14 | CATGGAGGGC | TTGCTCGAGG | ACTTCATGAA | GGTGCTAAGG | TCATTGAGAA | GCATGCTGCA | 177 |
|  |  | 200 | | 220 | | 240 |  |
| SEQ ID NO: 2 | CAGCTTTGTG | TGCTAGCAGA | GGACTGCGAC | CAGCCAGACT | ATGTCAAGCT | GGTCAAAGCT | 237 |
| SEQ ID NO: 23 | CAGCTTTGTG | TGCTAGCTGA | GGACTGTGAC | CAGCCAGATT | ACGTCAAACT | GGTGAAAGCA | 240 |
| SEQ ID NO: 11 | CAGCTTTGTG | TGTTAGCAGA | GGACTGTGAC | CAGCCAGATT | ATGTCAAATT | GGTCAAAGCG | 231 |
| SEQ ID NO: 12 | CAGCTTTGTG | TGCTAGCAGA | GGACTGTGAT | CAGCCAGATT | ATGTCAAACT | GGTGAAAGGA | 237 |
| SEQ ID NO: 13 | CAGCTTTGTG | TGTTAGCAGA | GGACTGTGAC | CAGCCAGATT | ATGTCAAATT | GGTCAAAGCA | 231 |
| SEQ ID NO: 14 | CAGCTTTGTG | TGCTAGCAGA | GGACTGTGAT | CAGCCAGATT | ATGTCAAACT | GGTGAAAGGA | 237 |
|  |  | 260 | | 280 | | 300 |  |
| SEQ ID NO: 2 | CTTTGTGCTG | ATCACAATGT | CAGTTTGATT | ACAGTTCCCA | ATGCAAAAAC | TCTTGGCGAA | 297 |
| SEQ ID NO: 23 | CTTTGTGCTG | ATCACAATGT | CAGTTTAATT | ACAGTTCCCA | ATGCAAAAAC | TCTTGGCGAA | 300 |
| SEQ ID NO: 11 | CTCTGTGCTG | ATCACAATGT | CAGTTTGATT | ACGGTTCCGA | ATGCAAAAAC | TCTTGGCGAA | 291 |
| SEQ ID NO: 12 | CTTTGTGCTG | ATCACAATGT | CAGTTTGATT | ACAGTTCCCA | ATGCAAAGAC | TCTTGGCGAA | 297 |
| SEQ ID NO: 13 | CTCTGTGCTG | ATCACAATGT | CAGTTTGATT | ACGGTCCCGA | ATGCAAAAAC | TCTTGGCGAA | 291 |
| SEQ ID NO: 14 | CTTTGTGCTG | ATCACAACGT | CAGTTTGATT | ACAGTTCCCA | ATGCAAAGAC | TCTTGGCGAA | 297 |
|  |  | 320 | | 340 | | 360 |  |
| SEQ ID NO: 2 | TGGGCTGGTT | TATGCAAAAT | TGATTCTGAA | GGGAAAGCAA | GGAAAGTTGT | TGGTTGTGGC | 357 |
| SEQ ID NO: 23 | TGGGCTGGTT | TATGCAAAAT | TGATTCTGAA | GGGAAAGCAA | GGAAGGTTGT | TGGTTGTGGC | 360 |
| SEQ ID NO: 11 | TGGGCTGGTT | TGTGTAAGAT | TGATTCTGAA | GGGAAAGCAA | GGAAGGTGGT | CGGCTGTGGC | 351 |
| SEQ ID NO: 12 | TGGGCTGGTT | TATGTAAGAT | TGATTCTGAA | GGTAAAGCAA | GGAAGGTTGT | TGGTTGTGGC | 357 |
| SEQ ID NO: 13 | TGGGCTGGTT | TGTGTAAGAT | TGATTCAGAA | GGGAAAGCAA | GGAAGGTGGT | CGGCTGCGGC | 351 |
| SEQ ID NO: 14 | TGGGCTGGTT | TATGTAAGAT | TGATTCTGAA | GGTAAAGCAA | GGAAGGTTGT | TGGTTGTGGC | 357 |
|  |  | 380 | | 400 | | 420 |  |
| SEQ ID NO: 2 | TGTGTTGTCG | TGAAGGATTA | TGGGGAAGAG | ACTGAGGGTC | TCCATATCGT | CCAGGAGTAC | 417 |
| SEQ ID NO: 23 | TGTGTTGTCG | TGAAGGATTA | TGGTGAAGAG | ACTGAGGGTC | TCCATATCGT | CCAAGAGTAC | 420 |
| SEQ ID NO: 11 | TGTGTTGTTG | TGAAGGATTA | CGGAGAAGAG | ACTGAGGGTC | TGCATATTGT | CCAAGAGTAC | 411 |
| SEQ ID NO: 12 | TGTGTTGTCG | TGAAGGATTA | CGGTGAAGAG | ACCGAGGGTC | TCCATATCGT | CCAAGAATAT | 417 |
| SEQ ID NO: 13 | TGTGTTGTTG | TGCAGGATTA | CGGAGAAGAG | ACTGAGGGTC | TGCATATTGT | CCAAGAGTAC | 411 |
| SEQ ID NO: 14 | TGTGTTGTCG | TGAAGGATTA | CGGTGAAGAG | ACTGAGGGTC | TCCATATCGT | CCAAGAGTAT | 417 |

| SEQ ID NO: 2 | GTGAAGTCTC | ATTAA | 432 |
|---|---|---|---|
| SEQ ID NO: 23 | GTGAAGTCTC | ATTAA | 435 |
| SEQ ID NO: 11 | GTGAAGTCCC | ATTAA | 426 |
| SEQ ID NO: 12 | GTGAAGTCTC | ATTAG | 432 |
| SEQ ID NO: 13 | GTGAAGTCCC | ATTAA | 426 |
| SEQ ID NO: 14 | GTGAAGTCTC | ATTAG | 432 |

FIGURE 1

```
                        20                    40                      60
SEQ ID NO:3   MSGEDAAVPV VAA-ETPAPA LGEPMDIMTA LQLVLRKSKA HGGLARGLHE GAKVIEKHAA
SEQ ID NO:24  MSGEDAAVPV VAAAETPAPA LGEPMDIMTA LQLVLKKSKA HGGLARGLHE GAKVIEKHAA
SEQ ID NO:15  MSGEDVAVA- ---VAEAPAPS LGEPMDIMTA LQLVLRKSKA HGGLSRGLHE GAKVIEKHAA
SEQ ID NO:16  MSGEDAAV-A VPAVETPSPA LGEPMDIMTA LQLVLRKSKA HGGLARGLHE GAKVIEKHAA
SEQ ID NO:17  MSGEDAAV-A VPAVETPAPA LGEPMDIMTA LQLVLRKSKA HGGLARGLHE GAKVIEKHAA
SEQ ID NO:18  MSGEDVAV-- -AVAEAPAPA LGEPMDIMTA LQLVLRKSRA HGGLSRGLHE GAKVIEKHAA
                        80                    100                     120
SEQ ID NO:3   QLCVLAEDCD QPDYVKLVKA LCADHNVSLI TVPNAKTLGE WAGLCKIDSE GKARKVVGCG
SEQ ID NO:24  QLCVLAEDCD QPDYVKLVKA LCADHNVSLI TVPNAKTLGE WAGLCKIDSE GKARKVVGCG
SEQ ID NO:15  QLCVLAEDCD QPDYVKLVKA LCADHNVSLI TVPNAKTLGE WAGLCKIDSE GKARKVVGCG
SEQ ID NO:16  QLCVLAEDCD QPDYVKLVKG LCADHNVSLI TVPNAKTLGE WAGLCKIDSE GKARKVVGCG
SEQ ID NO:17  QLCVLAEDCD QPDYVKLVKG LCADHNVSLI TVPNAKTLGE WAGLCKIDSE GKARKVVGCG
SEQ ID NO:18  QLSVLAEDCD QPDYVKLVKA LCADHNVSLI TVPNAKTLGE WAGLCKIDSE GKARKVVGCG
                        140
SEQ ID NO:3   CVVVKDYGEE TEGLHIVQEY VKSH 143
SEQ ID NO:24  CVVVKDYGEE TEGLHIVQEY VKSH 144
SEQ ID NO:15  CVVVKDYGEE TEGLHIVQEY VKSH 141
SEQ ID NO:16  CVVVKDYGEE TEGLHIVQEY VKSH 143
SEQ ID NO:17  CVVVKDYGEE TEGLHIVQEY VKSH 143
SEQ ID NO:18  CVVVQDYGEE TEGLHIVQEY VKSH 141
```

FIGURE 2

SEQUENCE LISTING

```
Sequence total quantity: 24
SEQ ID NO: 1            moltype = DNA  length = 1043
FEATURE                 Location/Qualifiers
source                  1..1043
                        mol_type = genomic DNA
                        organism = Nicotiana tabacum
SEQUENCE: 1
tgactagctc gtcgtattgt gggatgacga tacatcacca gaatcagtta gcatgatacg   60
cagctggaat acctcatcaa gatcaaaagc tggagctccc cgcggtggcg gccgctctag   120
aactagtgga tcccccgggc tgcaggaatt cggcacgagg cattactgca actcaaagca   180
gattgcgtcg tctctaaatt ttaaggttgc tgtgtttttt tgggtttaac atttaccaag   240
aaagaaatat gtcaggagag gatgctgctg ttcctgttgt tgctgccgag actcctgctc   300
cagcacttgg ggagcccatg gacatcatga ccgctctgca gctggtgctc aggaagtcta   360
aagctcatgg aggacttgct cgaggactcc atgaaggtgc taaggtgatt gagaagcatg   420
ctgcgcagct ttgtgtgcta gcagaggact gcgaccagcc agactatgtc aagctggtca   480
aagctctttg tgctgatcac aatgtcagtt tgattacagt tcccaatgca aaaactcttg   540
gcgaatgggc tggtttatgc aaaattgatt ctgaagggaa agcaaggaaa gttgttggtt   600
gtggctgtgt tgtcgtgaag gattatgggg aagagactga gggtctccat atcgtccagg   660
agtacgtgaa gtctcattaa atataaggtt gagatggagc tttaggggac tatgaggcta   720
gataagtctg agacggagct ttaggggga actatgaagc tagagattcc atgagactat   780
cttttggca tttatttaga gttgaatttt tgagatttca aactatgttc ccttattatt   840
gtgttacttc aagttttgtt ttaccttctg ggaagatcta atagtttgaa actgccgtct   900
agtttaaaaa aaaaaaaaaa aaaactcgag gggggcccg gtacccaatt ctgagtcgat   960
tacatcctgc gtcgttacac gtctgactga aactgcgtac actatcgctg aacatcccct   1020
ttcgcactgg gtagcgaaag ctc                                          1043

SEQ ID NO: 2            moltype = DNA  length = 432
FEATURE                 Location/Qualifiers
source                  1..432
                        mol_type = unassigned DNA
                        organism = Nicotiana tabacum
```

```
SEQUENCE: 2
atgtcaggag aggatgctgc tgttcctgtt gttgctgccg agactcctgc tccagcactt    60
ggggagccca tggacatcat gaccgctctg cagctggtgc tcaggaagtc taaagctcat   120
ggaggacttg ctcgaggact ccatgaaggt gctaaggtga ttgagaagca tgctgcgcag   180
ctttgtgtgc tagcagagga ctgcgaccag ccagactacg tcaagctggt caaagctctt   240
tgtgctgatc acaatgtcag tttgattaca gttcccaatg caaaaactct ggcgaatgg    300
gctggtttat gcaaaattga ttctgaaggg aaagcaagga agttgttgg ttgtggctgt    360
gttgtcgtga aggattatgg ggaagagact gagggtctcc atatcgtcca ggagtacgtg   420
aagtctcatt aa                                                       432

SEQ ID NO: 3             moltype = AA   length = 143
FEATURE                  Location/Qualifiers
source                   1..143
                         mol_type = protein
                         organism = Nicotiana tabacum
SEQUENCE: 3
MSGEDAAVPV VAAETPAPAL GEPMDIMTAL QLVLRKSKAH GGLARGLHEG AKVIEKHAAQ    60
LCVLAEDCDQ PDYVKLVKAL CADHNVSLIT VPNAKTLGEW AGLCKIDSEG KARKVVGCGC   120
VVVKDYGEET EGLHIVQEYV KSH                                           143

SEQ ID NO: 4             moltype = DNA   length = 502
FEATURE                  Location/Qualifiers
misc_feature             1..502
                         note = synthetic oligonucleotide
source                   1..502
                         mol_type = other DNA
                         organism = synthetic construct
SEQUENCE: 4
cgaggcatta ctgcaactca agcagattg cgtcgtctct aaattttaag gttgctgtgt     60
tttttgggt ttaacattta ccaagaaaga aatatgtcag gagaggatgc tgctgttcct   120
gttgttgctg ccgagactcc tgctccagca cttggggagc ccatggacat catgaccgct   180
ctgcagctgg tgctcaggaa gtctaaagct catggaggac ttgctcgagg actccatgaa   240
ggtgctaagg tgattgagaa gcatgctgcg cagctttgtg tgctagcaga ggactgcgac   300
cagccagact atgtcaagct ggtcaaagct cttgtgctg atcacaatgt cagttttgatt  360
acagttccca atgcaaaaac tcttggcgaa tgggctggtt tatgcaaaat tgattctgaa   420
gggaaagcaa ggaaagttgt tggttgtggc tgtgttgtcg tgaaggatta tggggaagag   480
actgagggtc tccatatcgt cc                                            502

SEQ ID NO: 5             moltype = DNA   length = 502
FEATURE                  Location/Qualifiers
misc_feature             1..502
                         note = synthetic oligonucleotide
source                   1..502
                         mol_type = other DNA
                         organism = synthetic construct
SEQUENCE: 5
ggacgatatg gagaccctca gtctcttccc cataatcctt cacgacaaca cagccacaac    60
caacaacttt ccttgctttc ccttcagaat caattttgca taaaccagcc cattcgccaa   120
gagttttgc attgggaact gtaatcaaac tgacattgtg atcagcacaa agagctttga   180
ccagcttgac atagtctggc tggtcgcagt cctctgctag cacacaaagc tgcgcagcat   240
gcttctcaat caccttagca ccttcatgga gtcctcgagc aagtcctcca tgagcttttga  300
acttcctgag caccagctgc agagcggtca tgatgtccat gggctcccca agtgctggag   360
caggagtctc ggcagcaaca acaggaacag cagcatcctc tcctgacata tttctttctt   420
ggtaaatgtt aaacccaaaa aaacacagca accttaaaat ttagagacga cgcaatctgc   480
tttgagttgc agtaatgcct cg                                            502

SEQ ID NO: 6             moltype = DNA   length = 672
FEATURE                  Location/Qualifiers
misc_feature             1..672
                         note = synthetic oligonucleotide
source                   1..672
                         mol_type = other DNA
                         organism = synthetic construct
SEQUENCE: 6
gaattcggtg agttcccccc tcctcccctt tcactttgt ttgttggttt ctaagtgctc     60
tttcaattta gaggttgatg ttgggaaata attaaacaat actcttgttt tctaaaattt   120
cttgaaaact acaatgtcta tagaggcaat atatttgctt ctaaacgttg acggttttgc   180
aagtcttgcg gaggagcttt gatccagtgt taaagaaata tatcatgtct cttattcatc   240
ctcccttttct ttccttttgtg ttttgcttca ctcctgggt ttcaactttt tctttccgt   300
ttaaccttc cttttttctg caggatgaa cttcaaatta ctttaaagga ctgatgctcc    360
ttctctgcta ttgatagttg ctgcaagttt ctttgtgcat atagatccag agtctatacg   420
taagttgtgt ttcttttcg tgaaattacc atatgacatt gacagctcct ggtcttcgtt    480
ttatttattc tttttggtgt tccttttaacc gataacatct gttattattt cactgttaca   540
ctaatctgct ttgcttatgg tcagtcagtt tagcattaga ttagataacc agttaaccat   600
tttgggtctc gttaacgtaa tattgtattg ataactacct tatcatatat atatctctgt   660
tttagtgaat tc                                                       672

SEQ ID NO: 7             moltype = DNA   length = 28
FEATURE                  Location/Qualifiers
```

```
misc_feature          1..28
                      note = synthetic oligonucleotide
source                1..28
                      mol_type = other DNA
                      organism = synthetic construct
SEQUENCE: 7
attctagacg aggcattact gcaactca                                          28

SEQ ID NO: 8          moltype = DNA  length = 28
FEATURE               Location/Qualifiers
misc_feature          1..28
                      note = synthetic oligonucleotide
source                1..28
                      mol_type = other DNA
                      organism = synthetic construct
SEQUENCE: 8
ataagcttgg acgatatgga gaccctca                                          28

SEQ ID NO: 9          moltype = DNA  length = 28
FEATURE               Location/Qualifiers
misc_feature          1..28
                      note = synthetic oligonucleotide
source                1..28
                      mol_type = other DNA
                      organism = synthetic construct
SEQUENCE: 9
atgagctccg aggcattact gcaactca                                          28

SEQ ID NO: 10         moltype = DNA  length = 28
FEATURE               Location/Qualifiers
misc_feature          1..28
                      note = synthetic oligonucleotide
source                1..28
                      mol_type = other DNA
                      organism = synthetic construct
SEQUENCE: 10
atggattcgg acgatatgga gaccctca                                          28

SEQ ID NO: 11         moltype = DNA  length = 426
FEATURE               Location/Qualifiers
source                1..426
                      mol_type = unassigned DNA
                      organism = Solanum lycopersicum
SEQUENCE: 11
atgtcgggag aggatgttgc tgttgctgtt gccgaggctc ctgctccatc acttggagag       60
cccatggaca tcatgactgc tttgcagctg gtgctgagga agtctaaggc tcatggaggc      120
ctctctcggg gactacatga aggtgcaaag gtgattgaga agcatgctgc acagctttgt      180
gtgttagcag aggactgtga ccagccagat tatgtcaaat tggtcaaagc gctctgtgct      240
gatcacaatg tcagtttgat tacggttccg aatgcaaaaa ctcttggcga atgggctggt      300
ttgtgtaaga ttgattctga agggaaagca aggaaggtgg tcggctgtgg ctgtgttgtt      360
gtgaaggatt acggagaaga gactgagggt ctgcatattg tccaagagta cgtgaagtcc      420
cattaa                                                                 426

SEQ ID NO: 12         moltype = DNA  length = 432
FEATURE               Location/Qualifiers
source                1..432
                      mol_type = unassigned DNA
                      organism = Solanum tuberosum
SEQUENCE: 12
atgtctggag aggatgctgc tgttgctgtt cccgctgttg agactccttc tccagcactt       60
ggagagccca tggatatcat gactgctcta cagctggtgc tcaggaagtc taaagctcat      120
ggagggcttg ctcgaggact tcatgaaggt gctaaggtca ttgagaagca tgctgcacag      180
ctttgtgtgc tagcagagga ctgtgatcag ccagattatg tcaaactggt gaaaggactt      240
tgtgctgatc acaatgtcag tttgattaca gttcccaatg caaagactct tggcgaattg      300
gctggtttat gtaagattga ttctgaaggt aaagcaagga aggttgttgg ttgtggctgt      360
gttgtcgtga aggattacgg tgaagagacc gagggtctcc atatcgtcca agaatatgtg      420
aagtctcatt ag                                                          432

SEQ ID NO: 13         moltype = DNA  length = 426
FEATURE               Location/Qualifiers
source                1..426
                      mol_type = unassigned DNA
                      organism = Solanum tuberosum
SEQUENCE: 13
atgtcaggag aggatgttgc tgttgctgtt gccgaggctc ctgctccagc acttggagag       60
cccatggaca tcatgactgc tttgcagctg gtgctgagga agtctagagc tcatggaggc      120
ctctctcggg gactacatga aggtgcaaag gtgattgaga agcatgctgc acagctttgt      180
gtgttagcag aggactgtga ccagccagat tatgtcaaat tggtcaaagc actctgtgct      240
gatcacaatg tcagtttgat tacggtcccg aatgcaaaaa ctcttggcga atgggctggt      300
```

```
ttgtgtaaga ttgattcaga agggaaagca aggaaggtgg tcggctgcgg ctgtgttgtt      360
gtgcaggatt acggagaaga gactgagggt ctgcatattg tccaagagta cgtgaagtcc      420
cattaa                                                                 426

SEQ ID NO: 14            moltype = DNA  length = 432
FEATURE                  Location/Qualifiers
source                   1..432
                         mol_type = unassigned DNA
                         organism = Solanum lycopersicum
SEQUENCE: 14
atgtctggag aggatgctgc tgttgctgtt cccgctgtcg agactcctgc tccagcactt       60
ggagagccca tggatatcat gactgctctg cagctggtgc tcaggaagtc taaagctcat      120
ggagggcttg ctcgaggact tcatgaaggt gctaaggtca ttgagaagca tgctgcacag      180
ctttgtgtgc tagcaggaga ctgtgatcag ccagattatg tcaaactggt gaaaggactt      240
tgtgctgatc acaacgtcag tttgattaca gttcccaatg caaagactct ggcgaatgg      300
gctggtttat gtaagattga ttctgaaggt aaagcaagga aggttgttgg ttgtggctgt      360
gttgtcgtga aggattacgg tgaagagact gagggtctcc atatcgtcca agagtatgtg      420
aagtctcatt ag                                                          432

SEQ ID NO: 15            moltype = AA  length = 141
FEATURE                  Location/Qualifiers
source                   1..141
                         mol_type = protein
                         organism = Solanum lycopersicum
SEQUENCE: 15
MSGEDVAVAV AEAPAPSLGE PMDIMTALQL VLRKSAHGG LSRGLHEGAK VIEKHAAQLC         60
VLAEDCDQPD YVKLVKALCA DHNVSLITVP NAKTLGEWAG LCKIDSEGKA RKVVGCGCVV      120
VKDYGEETEG LHIVQEYVKS H                                                141

SEQ ID NO: 16            moltype = AA  length = 143
FEATURE                  Location/Qualifiers
source                   1..143
                         mol_type = protein
                         organism = Solanum tuberosum
SEQUENCE: 16
MSGEDAAVAV PAVETPSPAL GEPMDIMTAL QLVLRKSKAH GGLARGLHEG AKVIEKHAAQ        60
LCVLAEDCDQ PDYVKLVKGL CADHNVSLIT VPNAKTLGEW AGLCKIDSEG KARKVVGCGC      120
VVVKDYGEET EGLHIVQEYV KSH                                              143

SEQ ID NO: 17            moltype = AA  length = 143
FEATURE                  Location/Qualifiers
source                   1..143
                         mol_type = protein
                         organism = Solanum lycopersicum
SEQUENCE: 17
MSGEDAAVAV PAVETPAPAL GEPMDIMTAL QLVLRKSKAH GGLARGLHEG AKVIEKHAAQ        60
LCVLAEDCDQ PDYVKLVKGL CADHNVSLIT VPNAKTLGEW AGLCKIDSEG KARKVVGCGC      120
VVVKDYGEET EGLHIVQEYV KSH                                              143

SEQ ID NO: 18            moltype = AA  length = 141
FEATURE                  Location/Qualifiers
source                   1..141
                         mol_type = protein
                         organism = Solanum tuberosum
SEQUENCE: 18
MSGEDVAVAV AEAPAPALGE PMDIMTALQL VLRKSRAHGG LSRGLHEGAK VIEKHAAQLS        60
VLAEDCDQPD YVKLVKALCA DHNVSLITVP NAKTLGEWAG LCKIDSEGKA RKVVGCGCVV      120
VQDYGEETEG LHIVQEYVKS H                                                141

SEQ ID NO: 19            moltype = DNA  length = 53
FEATURE                  Location/Qualifiers
misc_feature             1..53
                         note = synthetic oligonucleotide
source                   1..53
                         mol_type = other DNA
                         organism = synthetic construct
SEQUENCE: 19
tgtcaggaga ggatgctgct gttcctgttg ttgctgccga gactcctgct cca              53

SEQ ID NO: 20            moltype = DNA  length = 71
FEATURE                  Location/Qualifiers
misc_feature             1..71
                         note = synthetic oligonucleotide
source                   1..71
                         mol_type = other DNA
                         organism = synthetic construct
SEQUENCE: 20
tgctgccgag actcctgctc cagcacttgg ggagcccatg acatcatga ccgctctgca        60
gctggtgctc a                                                            71
```

```
SEQ ID NO: 21          moltype = DNA  length = 56
FEATURE                Location/Qualifiers
misc_feature           1..56
                       note = synthetic oligonucleotide
source                 1..56
                       mol_type = other DNA
                       organism = synthetic construct
SEQUENCE: 21
tgtcaggaga ggatgctgct gttcctgttg tcgctgctgc cgagactcct gctcca     56

SEQ ID NO: 22          moltype = DNA  length = 71
FEATURE                Location/Qualifiers
misc_feature           1..71
                       note = synthetic oligonucleotide
source                 1..71
                       mol_type = other DNA
                       organism = synthetic construct
SEQUENCE: 22
tgctgccgag actcctgctc cagcacttgg ggagcccatg gacatcatga ccgctctgca  60
gctggtgctc a                                                       71

SEQ ID NO: 23          moltype = DNA  length = 435
FEATURE                Location/Qualifiers
source                 1..435
                       mol_type = unassigned DNA
                       organism = Nicotiana tabacum
SEQUENCE: 23
atgtcaggag aggatgctgc tgttcctgtt gtcgctgctg ccgagactcc tgctccagca  60
cttggggagc ccatggacat catgaccgca ctacagctgg tgctaaagaa gtctaaagct  120
catggaggac ttgctcgagg actccatgaa ggtgctaagg tgattgagaa gcatgctgca  180
cagctttgtg tgctagctga ggactgtgac cagccagatt acgtcaaact ggtgaaagca  240
ctttgtgctg atcacaatgt cagtttaatt acagttccca atgcaaaaac tcttggcgaa  300
tgggctggtt tatgcaaaat tgattctgaa gggaaagcaa ggaaggttgt tggttgtggc  360
tgtgttgtcg tgaaggatta tggtgaagag actgagggtc tccatatcgt ccaagagtac  420
gtgaagtctc attaa                                                   435

SEQ ID NO: 24          moltype = AA  length = 144
FEATURE                Location/Qualifiers
source                 1..144
                       mol_type = protein
                       organism = Nicotiana tabacum
SEQUENCE: 24
MSGEDAAVPV VAAAETPAPA LGEPMDIMTA LQLVLKKSKA HGGLARGLHE GAKVIEKHAA   60
QLCVLAEDCD QPDYVKLVKA LCADHNVSLI TVPNAKTLGE WAGLCKIDSE GKARKVVGCG   120
CVVVKDYGEE TEGLHIVQEY VKSH                                          144
```

TOBACCO HAVING ALTERED LEAF PROPERTIES AND METHODS OF MAKING AND USING

CROSS-REFERENCE TO RELATED APPLICATIONS AND INCORPORATION OF SEQUENCE LISTING

This application is a continuation of U.S. patent application Ser. No. 17/096,213, filed Nov. 12, 2020, which is a continuation of U.S. patent application Ser. No. 16/149,456, filed Oct. 2, 2018 (now U.S. Pat. No. 10,851,384, issued Dec. 1, 2020), which is a continuation of U.S. patent application Ser. No. 14/789,177, filed Jul. 1, 2015 (now U.S. Pat. No. 10,113,174, issued Oct. 30, 2018), which claims the benefit of U.S. Provisional Application No. 62/019,936, filed Jul. 2, 2014, which is incorporated by reference in its entirety herein. A sequence listing contained in the file named "P34630US04_SL.XML" which is 32,768 bytes (measured in MS-Windows®) and created on Aug. 30, 2022, is filed electronically herewith and incorporated by reference in its entirety.

TECHNICAL FIELD

This disclosure generally relates to transgenic or mutant *Nicotiana tabacum* plants and methods of making and using such plants.

BACKGROUND

Nicotine is an abundant alkaloid (90-95%) present in cultivated tobacco. The remaining alkaloid fraction is primarily comprised of three additional alkaloids: nornicotine, anabasine, and anatabine. This disclosure describes methods of modulating the expression and/or activity of PR50 to thereby reduce the amount of nicotine and other alkaloids in the leaf.

SUMMARY

Provided herein are transgenic tobacco plants containing a PR50 RNAi and tobacco plants having a mutation in the gene encoding PR50, as well as methods of making and using such plants.

In one aspect, a RNA nucleic acid molecule is provided that includes a first nucleic acid between 15 and 500 nucleotides in length and a second nucleic acid between 15 and 500 nucleotides in length. Generally, the first nucleic acid has a region of complementarity to the second nucleic acid, and the first nucleic acid comprises at least 15 contiguous nucleotides of the sequence shown in SEQ ID NO:1.

In some embodiments, the second nucleic acid hybridizes under stringent conditions to a portion of the sequence shown in SEQ ID NO:1. In some embodiments, the region of complementarity is at least 19 nucleotides in length. In some embodiments, the region of complementarity is at least 100 nucleotides in length. In some embodiments, a nucleic acid molecule as described herein can further include a spacer nucleic acid between the first nucleic acid and the second nucleic acid.

In another aspect, a construct is provided that includes a first RNA nucleic acid molecule having a length of 15 to 500 nucleotides and having at least 95% sequence identity to a nucleic acid shown in SEQ ID NO:1. In some embodiments, the construct can further include a second RNA nucleic acid molecule that has complementarity to the first RNA nucleic acid molecule. In some embodiments, the construct can further include a spacer nucleic acid between the first and second RNA nucleic acid molecule.

In still another aspect, a method of making a *Nicotiana tabacum* plant is provided. Such a method typically includes transforming *N. tabacum* cells with a nucleic acid molecule as described herein or a construct as described herein to produce transgenic *N. tabacum* cells; regenerating transgenic *N. tabacum* plants from the transgenic *N. tabacum* cells; and selecting at least one transgenic *N. tabacum* plant that comprises the nucleic acid molecule or the construct.

In some embodiments, such a method further includes identifying at least one transgenic *N. tabacum* plant having reduced amount of nicotine relative to a *N. tabacum* plant not transformed with the nucleic acid molecule. In some embodiments, such a method further includes identifying at least one transgenic *N. tabacum* plant that, when material from the at least one transgenic *N. tabacum* plant is cured, exhibits a reduced amount of at least one TSNA relative to cured material from a *N. tabacum* plant not transformed with the nucleic acid molecule. In some embodiments, leaf from the selected transgenic *N. tabacum* plant exhibits comparable or better quality than leaf from the non-transformed *N. tabacum* plant. In some embodiments, the *N. tabacum* plant is a Burley type, a dark type, a flue-cured type, or an Oriental type.

In another aspect, a transgenic *Nicotiana tabacum* plant is provided that includes a vector. Generally, the vector includes a RNA nucleic acid molecule having a length of 15 to 500 nucleotides and having at least 95% sequence identity to a PR50 nucleic acid shown in SEQ ID NO:1. In some embodiments, the plant exhibits reduced amount of nicotine in the leaf relative to leaf from a *N. tabacum* plant lacking the nucleic acid molecule. In some embodiments, when material from the at least one transgenic *N. tabacum* plant is cured, it exhibits a reduced amount of at least one TSNA relative to cured material from a *N. tabacum* plant lacking the nucleic acid molecule. In some embodiments, leaf from the plant exhibits comparable or better quality than leaf from a *N. tabacum* plant lacking the nucleic acid molecule.

In still another aspect, cured leaf is provided from any of the transgenic *N. tabacum* plants described herein. In yet another aspect, a tobacco product is provided that includes cured leaf as described herein. Representative tobacco products include, without limitation, cigarettes, smokeless tobacco products, tobacco-derived nicotine products (e.g., tobacco-derived nicotine pieces for use in the mouth), cigarillos, non-ventilated recess filter cigarettes, vented recess filter cigarettes, cigars, electronic cigarettes, electronic cigars, electronic cigarillos, e-vapor devices, snuff, pipe tobacco, cigar tobacco, cigarette tobacco, chewing tobacco, leaf tobacco, shredded tobacco, and cut tobacco.

In one aspect, a method of making a *Nicotiana tabacum* plant is provided. Such a method typically includes inducing mutagenesis in *N. tabacum* cells to produce mutagenized *N. tabacum* cells; obtaining one or more *N. tabacum* plants from the mutagenized *N. tabacum* cells; and identifying at least one of the *N. tabacum* plants that comprises a mutated PR50 sequence.

In some embodiments, such a method can further include identifying at least one of the *N. tabacum* plants that exhibits reduced amounts of nicotine relative to a *N. tabacum* plant lacking a mutated PR50. In some embodiments, such a method can further include identifying at least one of the *N. tabacum* plants that, when material from the at least one plant is cured, exhibits a reduced amount of at least one TSNA relative to cured material from a *N. tabacum* plant lacking a mutated PR50. In some embodiments, leaf from the mutant *N. tabacum* plant exhibits comparable or better quality than leaf from the plant lacking a mutated PR50 sequence. In some embodiments, the *N. tabacum* plant is a Burley type, a dark type, a flue-cured type, or an Oriental type.

In another aspect, a variety of *Nicotiana tabacum* is provided. Generally, the variety includes plants having a mutation in an endogenous nucleic acid, where the wild type endogenous nucleic acid encodes the PR50 sequence shown in SEQ ID NO:2. In some embodiments, leaf from the mutant plants exhibits a reduced amount of nicotine relative to leaf from a plant lacking the mutation. In some embodiments, material from the mutant plants, when cured, exhibits a reduced amount of at least one TSNA relative to cured material from a plant lacking the mutation. In some embodiments, leaf from the mutant *N. tabacum* plant exhibits comparable or better quality than leaf from the plant lacking a mutated PR50 sequence.

In still another aspect, cured leaf is provided from any of the *N. tabacum* varieties described herein. In yet another aspect, a tobacco product is provided that includes cured leaf described herein. Representative tobacco products include, without limitation, cigarettes, smokeless tobacco products, tobacco-derived nicotine products (e.g., tobacco-derived nicotine pieces for use in the mouth), cigarillos, non-ventilated recess filter cigarettes, vented recess filter cigarettes, cigars, electronic cigarettes, electronic cigars, electronic cigarillos, e-vapor devices, snuff, pipe tobacco, cigar tobacco, cigarette tobacco, chewing tobacco, leaf tobacco, shredded tobacco, and cut tobacco.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 1 is an alignment of the PR50 nucleotide sequence (SEQ ID NO: 2) and its homologs: PR50 homologue (SEQ ID NO: 23). Tomato 40S ribosomal protein S12-like (SEQ ID NO: 11) Potato 40S ribosomal protein 512-like (SEQ ID NO: 12). Potato 405 ribosomal protein S12-like isoform 1 (SEQ ID NO: 13), and Tomato 40S ribosomal protein 512-like isoform 1 (SEQ ID NO: 14).

FIG. 2 is an alignment of the PR50 amino acid sequence (SEQ ID NO: 3) and its homologs: PR50 homologue (SEQ ID NO: 24), Tomato 405 ribosomal protein S12-like (SEQ ID NO: 15), Potato 40S ribosomal protein S12-like (SEC) ID NO: 16) Potato 40S ribosomal protein S12-like isoform 1 (SEQ ID NO: 17), and Tomato 40S ribosomal protein S12-like isoform 1 (SEQ ID NO: 18).

DETAILED DESCRIPTION

Figure 3:
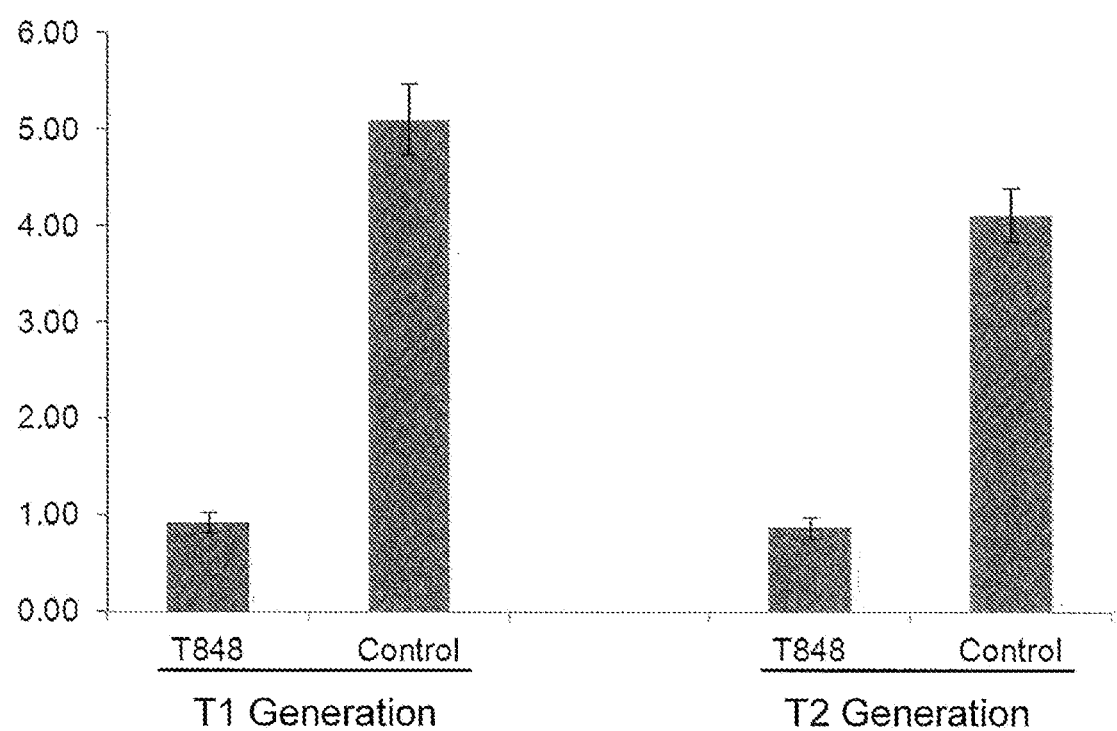
FIG. 3 is a graph showing the nicotine levels in T848 transgenic or control plants (T1 and T2 generations) following growth in the field.

PR50 is a cDNA that is differentially expressed in roots of *Nicotiana tabacum* cv Burley 21 during the early stages of alkaloid biosynthesis. See, for example, Wang et al., 2000, Plant Sci., 158:19-32. PR50 has about 88-93% sequence identity at the nucleic acid level, and 93-97% sequence identity at the amino acid level, to a 40S ribosomal protein from *Solanum* spp. The present disclosure describes several different approaches that can be used to significantly reduce nicotine levels in tobacco leaf while maintaining leaf quality.

PR50 Nucleic Acids and Polypeptides

A nucleic acid encoding PR50 from *N. tabacum* is shown in SEQ ID NO: 1 (genomic) and SEQ ID NO:2 (cDNA). A nucleic acid encoding a PR50 homologue from *N. tabacum* is shown in SEQ ID NO: 23 (cDNA). FIG. 1 is an alignment of the PR50 nucleotide sequence and several PR50 homologs. Unless otherwise specified, nucleic acids referred to herein can refer to DNA and RNA, and also can refer to nucleic acids that contain one or more nucleotide analogs or backbone modifications. Nucleic acids can be single stranded or double stranded, and linear or circular, both of which usually depend upon the intended use.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

The sequence of the PR50 polypeptide from *N. tabacum* is shown in SEQ ID NO: 3, and the sequence of the PR50 homologue polypeptide from *N. tabacum* is shown in SEQ ID NO:24. FIG. 2 is an alignment of the PR50 amino acid sequence and several PR50 homologs (SEQ ID NOs: 3 and 15-18 (top to bottom)). As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques well known in the art. For example, nucleic acids can be isolated using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Nucleic acids can be detected using any number of amplification techniques (see, e.g., *PCR Primer: A Laboratory Manual*, 1995, Dieffenbach & Dveksler, Eds., Cold Spring Harbor Laboratory Press, Cold Spring Harbor, NY; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid. Nucleic acids also can be detected using hybridization.

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is oftentimes accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

A construct, sometimes referred to as a vector, containing a nucleic acid (e.g., a coding sequence or a RNAi nucleic acid molecule) is provided. Constructs, including expression constructs (or expression vectors), are commercially available or can be produced by recombinant DNA techniques routine in the art. A construct containing a nucleic acid can have expression elements operably linked to such a nucleic acid, and further can include sequences such as those encoding a selectable marker (e.g., an antibiotic resistance gene). A construct can encode a chimeric or fusion polypeptide (i.e., a first polypeptide operatively linked to a second polypeptide). Representative first (or second) polypeptides are those that can be used in purification of the other (i.e., second (or first), respectively) polypeptide including, without limitation, 6×His tag or glutathione S-transferase (GST).

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame).

Constructs as described herein can be introduced into a host cell. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer. As used herein, "host cell" refers to the particular cell into which the nucleic acid is introduced and also includes the progeny or potential progeny of such a cell. A host cell can be any prokaryotic or eukaryotic cell. For example, nucleic acids can be introduced into bacterial cells such as *E. coli*, or into insect cells, yeast or mammalian cells (such as Chinese hamster ovary cells (CHO) or COS cells). Other suitable host cells are known to those skilled in the art.

RNA Interfering Nucleic Acids and Constructs Containing Same

RNA interference (RNAi), also called post-transcriptional gene silencing (PTGS), is a biological process in which RNA molecules inhibit gene expression, typically by causing the destruction of specific mRNA molecules. Without being bound by theory, it appears that, in the presence of an antisense RNA molecule that is complementary to an expressed message (i.e., a mRNA), the two strands anneal to generate long double-stranded RNA (dsRNA), which is digested into short (<30 nucleotide) RNA duplexes, known as small interfering RNAs (siRNAs), by an enzyme known as Dicer. A complex of proteins known as the RNA Induced Silencing Complex (RISC) then unwinds siRNAs, and uses one strand to identify and thereby anneal to other copies of the original mRNA. RISC cleaves the mRNA within the complementary sequence, leaving the mRNA susceptible to further degradation by exonucleases, which effectively silences expression of the encoding gene.

Several methods have been developed that take advantage of the endogenous machinery to suppress the expression of a specific target gene and a number of companies offer RNAi design and synthesis services (e.g., Life Technologies, Applied Biosystems). In transgenic plants, the use of RNAi can involve the introduction of long dsRNA (e.g., greater than 50 bps) or siRNAs (e.g., 12 to 23 bps) that have complementarity to the target gene, both of which are processed by the endogenous machinery. Alternatively, the use of RNAi can involve the introduction of a small hairpin RNA (shRNA); shRNA is a nucleic acid that includes the sequence of the two desired siRNA strands, sense and antisense, on a single strand, connected by a "loop" or "spacer" nucleic acid. When the shRNA is transcribed, the two complementary portions anneal intra-molecularly to form a "hairpin," which is recognized and processed by the endogenous machinery.

A RNAi nucleic acid molecule as described herein is complementary to at least a portion of a target mRNA (i.e., a PR50 mRNA), and typically is referred to as an "antisense strand". Typically, the antisense strand includes at least 15 contiguous nucleotides of the DNA sequence (e.g., the PR50 nucleic acid sequence shown in SEQ ID NO:1, 2 or 23); it would be appreciated that the antisense strand has the "RNA equivalent" sequence of the DNA (e.g., uracils instead of thymines; ribose sugars instead of deoxyribose sugars).

A RNAi nucleic acid molecule can be, for example, 15 to 500 nucleotides in length (e.g., 15 to 50, 15 to 45, 15 to 30, 16 to 47, 16 to 38, 16 to 29, 17 to 53, 17 to 44, 17 to 38, 18 to 36, 19 to 49, 20 to 60, 20 to 40, 25 to 75, 25 to 100, 28 to 85, 30 to 90, 15 to 100, 15 to 300, 15 to 450, 16 to 70, 16 to 150, 16 to 275, 17 to 74, 17 to 162, 17 to 305, 18 to 60, 18 to 75, 18 to 250, 18 to 400, 20 to 35, 20 to 60, 20 to 80, 20 to 175, 20 to 225, 20 to 325, 20 to 400, 20 to 475, 25 to 45, 25 to 65, 25 to 100, 25 to 200, 25 to 250, 25 to 300, 25 to 350, 25 to 400, 25 to 450, 30 to 280, 35 to 250, 200 to 500, 200 to 400, 250 to 450, 250 to 350, or 300 to 400 nucleotides in length).

In some embodiments, the "antisense strand" (e.g., a first nucleic acid) can be accompanied by a "sense strand" (e.g., a second nucleic acid), which is complementary to the antisense strand. In the latter case, each nucleic acid (e.g., each of the sense and antisense strands) can be between 15 and 500 nucleotides in length (e.g., between 15 to 50, 15 to 45, 15 to 30, 16 to 47, 16 to 38, 16 to 29, 17 to 53, 17 to 44, 17 to 38, 18 to 36, 19 to 49, 20 to 60, 20 to 40, 25 to 75, 25 to 100, 28 to 85, 30 to 90, 15 to 100, 15 to 300, 15 to 450, 16 to 70, 16 to 150, 16 to 275, 17 to 74, 17 to 162, 17 to 305, 18 to 60, 18 to 75, 18 to 250, 18 to 400, 20 to 35, 20 to 60, 20 to 80, 20 to 175, 20 to 225, 20 to 325, 20 to 400, 20 to 475, 25 to 45, 25 to 65, 25 to 100, 25 to 200, 25 to 250, 25 to 300, 25 to 350, 25 to 400, 25 to 450, 30 to 280, 35 to 250, 200 to 500, 200 to 400, 250 to 450, 250 to 350, or 300 to 400 nucleotides in length).

In some embodiments, a spacer nucleic acid, sometimes referred to as a loop nucleic acid, can be positioned between the sense strand and the antisense strand. In some embodiments, the spacer nucleic acid can be an intron (see, for example, Wesley et al., 2001, The Plant J., 27:581-90). In some embodiments, although not required, the intron can be functional (i.e., in sense orientation; i.e., spliceable) (see, for example, Smith et al., 2000, Nature, 407:319-20). A spacer nucleic acid can be between 20 nucleotides and 1000 nucleotides in length (e.g., 25-800, 25-600, 25-400, 50-750, 50-500, 50-250, 100-700, 100-500, 100-300, 250-700, 300-600, 400-700, 500-800, 600-850, or 700-1000 nucleotides in length).

In some embodiments, a construct can be produced by operably linking a promoter that is operable in plant cells; a DNA region, that, when transcribed, produces an RNA molecule capable of forming a hairpin structure; and a DNA region involved in transcription termination and polyadenylation. It would be appreciated that the hairpin structure has two annealing RNA sequences, where one of the annealing RNA sequences of the hairpin RNA structure includes a sense sequence identical to at least 20 consecutive nucleotides of the PR50 nucleotide sequence, and where the second of the annealing RNA sequences includes an antisense sequence that is identical to at least 20 consecutive nucleotides of the complement of the PR50 nucleotide sequence. In addition, as indicated herein, the DNA region can include an intron (e.g., a functional intron). When present, the intron generally is located between the two annealing RNA sequences in sense orientation such that it is spliced out by the cellular machinery (e.g., the splicesome). Such a construct can be introduced into one or more plant cells to reduce the phenotypic expression of a PR50 nucleic acid (e.g., a nucleic acid sequence that is normally expressed in a plant cell).

In some embodiments, a construct (e.g., an expression construct) can include an inverted-duplication of a segment of a PR50 gene, where the inverted-duplication of the PR50 gene segment includes a nucleotide sequence substantially identical to at least a portion of the PR50 gene and the complement of the portion of the PR50 gene. It would be appreciated that a single promoter can be used to drive expression of the inverted-duplication of the PR50 gene segment, and that the inverted-duplication typically contains at least one copy of the portion of the PR50 gene in the sense orientation. Such a construct can be introduced into one or more plant cells to delay, inhibit or otherwise reduce the expression of a PR50 gene in the plant cells.

The components of a representative RNAi nucleic acid molecule directed toward PR50 are shown in SEQ ID NO:4 (a sense strand to PR50); SEQ ID NO:5 (an antisense strand to PR50); and SEQ ID NO:6 (a spacer or loop sequence).

It would be appreciated by the skilled artisan that the region of complementarity, between the antisense strand of the RNAi and the mRNA or between the antisense strand of the RNAi and the sense strand of the RNAi, can be over the entire length of the RNAi nucleic acid molecule, or the region of complementarity can be less than the entire length of the RNAi nucleic acid molecule. For example, a region of complementarity can refer to, for example, at least 15 nucleotides in length up to, for example, 500 nucleotides in length (e.g., at least 15, 16, 17, 18, 19, 20, 25, 28, 30, 35, 49, 50, 60, 75, 80, 100, 150, 180, 200, 250, 300, 320, 385, 420, 435 nucleotides in length up to, e.g., 30, 35, 36, 40, 45, 49, 50, 60, 65, 75, 80, 85, 90, 100, 175, 200, 225, 250, 280, 300, 325, 350, 400, 450, or 475 nucleotides in length). In some embodiments, a region of complementarity can refer to, for example, at least 15 contiguous nucleotides in length up to, for example, 500 contiguous nucleotides in length (e.g., at least 15, 16, 17, 18, 19, 20, 25, 28, 30, 35, 49, 50, 60, 75, 80, 100, 150, 180, 200, 250, 300, 320, 385, 420, 435 nucleotides in length up to, e.g., 30, 35, 36, 40, 45, 49, 50, 60, 65, 75, 80, 85, 90, 100, 175, 200, 225, 250, 280, 300, 325, 350, 400, 450, or 475 contiguous nucleotides in length).

It would be appreciated by the skilled artisan that complementary can refer to, for example, 100% sequence identity between the two nucleic acids. In addition, however, it also would be appreciated by the skilled artisan that complementary can refer to, for example, slightly less than 100% sequence identity (e.g., at least 95%, 96%, 97%, 98%, or 99% sequence identity). In calculating percent sequence identity, two nucleic acids are aligned and the number of identical matches of nucleotides (or amino acid residues) between the two nucleic acids (or polypeptides) is determined. The number of identical matches is divided by the length of the aligned region (i.e., the number of aligned nucleotides (or amino acid residues)) and multiplied by 100 to arrive at a percent sequence identity value. It will be appreciated that the length of the aligned region can be a portion of one or both nucleic acids up to the full-length size of the shortest nucleic acid. It also will be appreciated that a single nucleic acid can align with more than one other nucleic acid and hence, can have different percent sequence identity values over each aligned region.

The alignment of two or more nucleic acids to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13):3497-500. ClustalW calculates the best match between a query and one or more subject sequences (nucleic acid or polypeptide), and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

The skilled artisan also would appreciate that complementary can be dependent upon, for example, the conditions under which two nucleic acids hybridize. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY; Sections 7.37-7.57, 9.47-9.57, 11.7-11.8, and 11.45-11.57). Sambrook et al. disclose suitable Southern blot conditions for oligonucleotide probes less than about 100 nucleotides (Sections 11.45-11.46). The Tm between a nucleic acid that is less than 100 nucleotides in length and a second nucleic acid can be calculated using the formula provided in Section 11.46. Sambrook et al. additionally disclose Southern blot conditions for oligonucleotide probes greater than about 100 nucleotides (see Sections 9.47-9.54). The Tm between a nucleic acid greater than 100 nucleotides in length and a second nucleic acid can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane. A nucleic acid molecule is deemed to hybridize to a nucleic acid, but not to another nucleic acid, if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantified directly on a membrane or from an autoradiograph using, for example, a PhosphorImager or a Densitometer (Molecular Dynamics, Sunnyvale, CA).

A construct (also known as a vector) containing a RNAi nucleic acid molecule is provided. Constructs, including expression constructs, are described herein and are known to those of skill in the art. Expression elements (e.g., promoters) that can be used to drive expression of a RNAi nucleic acid molecule are known in the art and include, without limitation, constitutive promoters such as, without limitation, the cassava mosaic virus (CsMVM) promoter, the cauliflower mosaic virus (CaMV) 35S promoter, the actin promoter, or the glyceraldehyde-3-phosphate dehydrogenase promoter, or tissue-specific promoters such as, without limitation, root-specific promoters such as the putrescine N-methyl transferase (PMT) promoter or the quinolinate phosphosibosyltransferase (QPT) promoter. It would be understood by a skilled artisan that a sense strand and an antisense strand can be delivered to and expressed in a target cell on separate constructs, or the sense and antisense strands can be delivered to and expressed in a target cell on a single construct (e.g., in one transcript). As discussed herein, a RNAi nucleic acid molecule delivered and expressed on a single strand also can include a spacer nucleic acid (e.g., a loop nucleic acid) such that the RNAi forms a small hairpin (shRNA).

Transgenic Plants and Methods of Making Transgenic Plants

Transgenic *N. tabacum* plants are provided that contain a transgene encoding at least one RNAi molecule, which, when transcribed, silences PR50 expression. As used herein, silencing can refer to complete elimination or essentially complete elimination of the PR50 mRNA, resulting in 100% or essentially 100% reduction (e.g., greater than 95% reduction; e.g., greater than 96%, 97%, 98% or 99% reduction) in the amount of PR50 polypeptide; silencing also can refer to partial elimination of the PR50 mRNA (e.g., eliminating about 5%, 10%, 15%, 20%, 25%, 30%, 35%, 40%, 45%, 50% or more of the PR50 mRNA), resulting in a reduction (e.g., about 5%, 10%, 15%, 20%, 25%, 30%, 35%, 40%, 45%, 50% or more, but not complete elimination) in the amount of the PR50 polypeptide.

A RNAi nucleic acid molecule can be transcribed using a plant expression vector. Methods of introducing a nucleic acid (e.g., a heterologous nucleic acid) into plant cells (e.g., *N. tabacum* cells) are known in the art and include, for example, particle bombardment, *Agrobacterium*-mediated transformation, microinjection, polyethylene glycol-mediated transformation (e.g., of protoplasts, see, for example, Yoo et al. (2007, *Nature Protocols*, 2(7):1565-72)), liposome-mediated DNA uptake, or electroporation.

Following transformation, the transgenic plant cells can be regenerated into transgenic tobacco plants. The regenerated transgenic plants can be screened for the presence of the transgene (e.g., a RNAi nucleic acid molecule) and/or one or more of the resulting phenotypes (e.g., reduced amount of PR50 mRNA or PR50 polypeptide, reduced activity of a PR50 polypeptide, reduced amount of nicotine or another alkaloid, and/or reduced amount of one or more TSNAs (in cured tobacco)) using methods described herein, and plants exhibiting the desired phenotype can be selected.

Methods of detecting alkaloids (e.g., nicotine) or TSNAs, and methods of determining the amount of one or more alkaloids or TSNAs are known in the art. For example, high performance liquid chromatography (HPLC)-mass spectroscopy (MS) (HPLC-MS) or high performance thin layer chromatography (HPTLC) can be used to detect the presence of one or more alkaloids and/or determine the amount of one or more alkaloids. In addition, any number of chromatography methods (e.g., gas chromatography/thermal energy analysis (GC/TEA), liquid chromatography/mass spectrometry (LC/MS), and ion chromatography (IC)) can be used to detect the presence of one or more TSNAs and/or determine the amount of one or more TSNAs.

As used herein, "reduced" or "reduction" refers to a decrease (e.g., a statistically significant decrease), in green leaf or cured leaf, of/in one or more of the following: a) the amount of PR50 mRNA; b) the amount of PR50 polypeptide; c) the activity of the PR50 polypeptide; d) the amount of nicotine or another alkaloid. In addition, "reduced" or "reduction" refers to a decrease (e.g., a statistically significant decrease), in cured leaf, in the amount of one or more tobacco-specific nitrosamines (TSNAs; e.g., N'-nitrosonornicotine (NNN), 4-(methylnitrosoamino)-1-(3-pyridyl)-1-butanone (NNK), N'-nitrosoanatabine (NAT), N'-nitrosoanabasine (NAB), and 4-(methylnitrosoamino)-1-(3-pyridyl)-1-butanal (NNAL)). As used herein, "reduced" or "reduction" refers to a decrease in any of the above by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the transgene. As used herein, statistical significance refers to a p-value of less than 0.05, e.g., a p-value of less than 0.025 or a p-value of less than 0.01, using an appropriate measure of statistical significance, e.g., a one-tailed two sample t-test.

Leaf from progeny plants also can be screened for the presence of the transgene and/or the resulting phenotype, and plants exhibiting the desired phenotype can be selected. As described herein, leaf from such transgenic plants exhibit a reduced amount of nicotine or another alkaloid, or, in cured tobacco, a reduced amount of one or more TSNAs (e.g., compared to leaf from a plant lacking or not transcribing the RNAi). As described herein, transcription of the transgene results in leaf that exhibits a reduced amount of nicotine or another alkaloid, or, in cured tobacco, a reduced amount of one or more TSNAs relative to leaf from a plant not transcribing the transgene. Leaf from regenerated transgenic plants can be screened for the amount of PR50, the amount of one or more other intermediates in the biosynthesis of nicotine, the amount of nicotine, or, in cured tobacco, the amount of one or more TSNAs, and plants having leaf that exhibit a reduced amount of nicotine or another alkaloid, or, in cured tobacco, a reduced amount of TSNAs, compared to the amount in a leaf from a corresponding non-transgenic plant, can be selected.

Transgenic plants exhibiting the desired phenotype can be used, for example, in a breeding program. Breeding is carried out using known procedures. Successful crosses yield $F_1$ plants that are fertile and that can be backcrossed with one of the parents if desired. In some embodiments, a plant population in the $F_2$ generation is screened for the presence of a transgene and/or the resulting phenotype using standard methods (e.g., amplification, hybridization and/or chemical analysis of the leaf). Selected plants are then crossed with one of the parents and the first backcross ($BC_1$) generation plants are self-pollinated to produce a $BC_1F_2$ population that is again screened. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the transgene and exhibits variant gene expression. Breeder's seed of the selected plant can be produced using standard methods including, for example, field testing and/or chemical analyses of leaf (e.g., cured leaf).

The result of a plant breeding program using the transgenic tobacco plants described herein are novel and useful varieties, lines, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individual with that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility where a transgene inhibits microsporogenesis and/or pollen formation, or self-incompatibility. Female parent plants having CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed set on the resulting male sterile plants.

Varieties and lines described herein can be used to form single-cross tobacco $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

The tobacco plants used in the methods described herein can be a Burley type, a dark type, a flue-cured type, a Maryland type, or an Oriental type. The tobacco plants used in the methods described herein typically are from *N. tabacum*, and can be from any number of *N. tabacum* varieties. A variety can be BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, Perique tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, or VA359.

Nucleic acids that confer traits such as herbicide resistance (sometimes referred to as herbicide tolerance), insect resistance, or stress tolerance, can also be present in the novel tobacco plants described herein. Genes conferring resistance to a herbicide that inhibits the growing point or meristem, such as an imidazolinone or a sulfonylurea, can be suitable. Exemplary genes in this category encode mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS), which is resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides.

Genes for resistance to glyphosate also are suitable. See, for example, U.S. Pat. Nos. 4,940,835 and 4,769,061. Such genes can confer resistance to glyphosate herbicidal compositions, including, without limitation, glyphosate salts such as the trimethylsulphonium salt, the isopropylamine salt, the sodium salt, the potassium salt and the ammonium salt. See, e.g., U.S. Pat. Nos. 6,451,735 and 6,451,732. Genes for resistance to phosphono compounds such as glufosinate ammonium or phosphinothricin, and pyridinoxy or phenoxy propionic acids and cyclohexones also are suitable. See, e.g., U.S. Pat. Nos. 5,879,903; 5,276,268; and 5,561,236; and European Application No. 0 242 246.

Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Pat. No. 6,084,155 and US 20010016956.

A number of genes are available that confer resistance to insects, for example, insects in the order Lepidoptera. Exemplary genes include those that encode truncated Cry1A(b) and Cry1A(c) toxins. See, e.g., genes described in U.S. Pat. Nos. 5,545,565; 6,166,302; and 5,164,180. See also, Vaeck et al., 1997, *Nature,* 328:33-37 and Fischhoff et al., 1987, *Nature Biotechnology,* 5:807-813. Particularly useful are genes encoding toxins that exhibit insecticidal activity against Manduca sexta (tobacco hornworm); *Heliothis virescens* Fabricius (tobacco budworm) and/or *S. litura* Fabricius (tobacco cutworm).

Mutant Plants and Methods of Making

Methods of making a *N. tabacum* plant having a mutation are known in the art. Mutations can be random mutations or targeted mutations. For random mutagenesis, cells (e.g., *N. tabacum* cells) typically are mutagenized using, for example, a chemical mutagen or ionizing radiation. Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN (see, for example, Li et al., 2011, *Nucleic Acids Res.,* 39(14):6315-25) or zinc-finger (see, for example, Wright et al., 2005, *The Plant* 1, 44:693-705). Whether random or targeted, a mutation can be a point mutation, an insertion, a deletion, a substitution, or combinations thereof, which are discussed in more detail below.

The resultant variety of *Nicotiana tabacum* includes plants having a mutation in an endogenous PR50 nucleic acid (e.g., SEQ ID NO: 1, 2, or 23) encoding a PR50 polypeptide sequence (e.g., SEQ ID NO: 3 or 24). A mutation in PR50 as described herein typically results in reduced expression or activity of PR50, which, in turn, results in a reduced amount of nicotine or another alkaloid, or, in cured tobacco, a reduced amount of one or more TSNAs in the mutant plant relative to a plant lacking the mutation.

As discussed herein, one or more nucleotides can be mutated to alter the expression and/or function of the encoded polypeptide, relative to the expression and/or function of the corresponding wild type polypeptide. It will be appreciated, for example, that a mutation in one or more of the highly conserved regions would likely alter polypeptide function, while a mutation outside of those highly conserved regions would likely have little to no effect on polypeptide function. In addition, a mutation in a single nucleotide can create a stop codon, which would result in a truncated polypeptide and, depending on the extent of truncation, loss of function.

Preferably, a mutation in a PR50 nucleic acid results in a tobacco plant that exhibits reduced expression or activity of PR50, a reduced amount of nicotine or another alkaloid, or, in cured tobacco, a reduced amount of one or more TSNAs. Suitable types of mutations in a PR50 coding sequence include, without limitation, insertions of nucleotides, deletions of nucleotides, or transitions or transversions in the wild-type PR50 coding sequence. Mutations in the coding sequence can result in insertions of one or more amino acids, deletions of one or more amino acids, and/or conservative or non-conservative amino acid substitutions in the encoded polypeptide. In some cases, the coding sequence of a PR50 comprises more than one mutation and/or more than one type of mutation.

Insertion or deletion of amino acids in a coding sequence, for example, can disrupt the conformation of the encoded polypeptide. Amino acid insertions or deletions also can disrupt sites important for recognition of binding ligand(s) or substrate(s) or for activity of the polypeptide. It is known in the art that the insertion or deletion of a larger number of contiguous amino acids is more likely to render the gene product non-functional, compared to a smaller number of inserted or deleted amino acids. In addition, one or more mutations (e.g., a point mutation) can change the localization of the PR50 polypeptide, introduce a stop codon to produce a truncated polypeptide, or disrupt an active site or domain (e.g., a catalytic site or domain, a binding site or domain) within the polypeptide.

A "conservative amino acid substitution" is one in which one amino acid residue is replaced with a different amino acid residue having a similar side chain (see, for example, Dayhoff et al. (1978, in *Atlas of Protein Sequence and Structure,* 5(Suppl. 3):345-352), which provides frequency tables for amino acid substitutions), and a non-conservative substitution is one in which an amino acid residue is replaced with an amino acid residue that does not have a similar side chain. Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Simply by way of example, a PR50 amino acid sequence (e.g., SEQ ID NO:3) can be mutated to change tyrosine to histidine, which may change the secondary structure of the polypeptide. In addition, a PR50 nucleic acid sequence (e.g., SEQ ID NO: 2) can be mutated to change the GG at position 299 and 300 to GA or AG; or the C at position 91, 133, 178, 208, or 409 to T, each of which would result in a stop codon. Such a mutation would significantly reduce or essentially eliminate the amount of PR50 mRNA or polypeptide or the activity of PR50 in the plant.

Following mutagenesis, $M_0$ plants are regenerated from the mutagenized cells and those plants, or a subsequent generation of that population (e.g., $M_1$, $M_2$, $M_3$, etc.), can be screened for those carrying a mutation in a PR50 sequence. Screening for plants carrying a mutation in a PR50 nucleic acid or polypeptide can be performed directly using methods routine in the art (e.g., hybridization, amplification, nucleic acid sequencing, peptide sequencing, combinations thereof) or by evaluating the phenotype (e.g., reduced expression or activity of PR50, reduced amounts of nicotine or another alkaloid, and/or reduced amounts of one or more TSNAs (in cured tobacco)). It would be understood that the phenotype of a mutant plant (e.g., reduced expression or activity of PR50, reduced amounts of nicotine or another alkaloid, and/or reduced amounts of one or more TSNAs (in cured tobacco)) would be compared to a corresponding plant (e.g., having the same varietal background) that lacks the mutation.

An $M_1$ tobacco plant may be heterozygous for a mutant allele and exhibit a wild type phenotype. In such cases, at least a portion of the first generation of self-pollinated progeny of such a plant exhibits a wild type phenotype. Alternatively, an $M_1$ tobacco plant may have a mutant allele and exhibit a mutant phenotype (e.g., reduced expression or activity of PR50, reduced amounts of nicotine or another alkaloid, and/or reduced amounts of one or more TSNAs (in cured tobacco)). Such plants may be heterozygous and exhibit a mutant phenotype due to a phenomenon such as dominant negative suppression, despite the presence of the wild type allele, or such plants may be homozygous due to independently induced mutations in both alleles.

As used herein, "reduced" or "reduction" refers to a decrease (e.g., a statistically significant decrease) in the expression or activity of PR50, or in the amount of nicotine or another alkaloid, in either green or cured tobacco, or in the amount of one or more TSNAs, in cured tobacco, by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the mutation. As used herein, statistical significance refers to a p-value of less than 0.05, e.g., a p-value of less than 0.025 or a p-value of less than 0.01, using an appropriate measure of statistical significance, e.g., a one-tailed two sample t-test.

A tobacco plant carrying a mutant allele can be used in a plant breeding program to create novel and useful lines, varieties and hybrids. Desired plants that possess the mutation can be backcrossed or self-pollinated to create a second population to be screened. Backcrossing or other breeding procedures can be repeated until the desired phenotype of the recurrent parent is recovered. DNA fingerprinting, SNP or similar technologies may be used in a marker-assisted selection (MAS) breeding program to transfer or breed mutant alleles into other tobaccos, as described herein.

In some embodiments, an $M_1$, $M_2$, $M_3$ or later generation tobacco plant containing at least one mutation is crossed with a second *Nicotiana tabacum* plant, and progeny of the cross are identified in which the mutation(s) is present. It will be appreciated that the second *Nicotiana tabacum* plant can be one of the species and varieties described herein. It will also be appreciated that the second *Nicotiana tabacum* plant can contain the same mutation as the plant to which it is crossed, a different mutation, or be wild type at the locus. Additionally or alternatively, a second tobacco line can exhibit a phenotypic trait such as, for example, disease resistance, high yield, high grade index, curability, curing quality, mechanical harvesting, holding ability, leaf quality, height, plant maturation (e.g., early maturing, early to medium maturing, medium maturing, medium to late maturing, or late maturing), stalk size (e.g., small, medium, or large), and/or leaf number per plant (e.g., a small (e.g., 5-10 leaves), medium (e.g., 11-15 leaves), or large (e.g., 16-21) number of leaves).

Cured Tobacco and Tobacco Products

The methods described herein allow for leaf constituents in a tobacco plant to be altered while still maintaining high leaf quality. As described herein, altering leaf constituents refers to reducing, in green or cured leaf, the amount of nicotine or another alkaloid, or reducing, in cured leaf, the amount of one or more TSNAs. As described herein, such methods can include the production of transgenic plants (using, e.g., RNAi or overexpression) or mutagenesis (e.g., random or targeted).

Leaf quality can be determined, for example, using an Official Standard Grade published by the Agricultural Marketing Service of the US Department of Agriculture (7 U.S.C. § 511); Legacy Tobacco Document Library (Bates Document #523267826/7833, Jul. 1, 1988, Memorandum on the Proposed Burley Tobacco Grade Index); and Miller et al., 1990, Tobacco Intern., 192:55-7. For dark-fired tobacco, leaves typically are obtained from stalk position C, and the average grade index determined based on Federal Grade and 2004 Price Support for Type 23 Western dark-fired tobacco.

Leaf from the tobacco described herein can be cured, aged, conditioned, and/or fermented. Methods of curing tobacco are well known and include, for example, air curing, fire curing, flue curing and sun curing. Aging also is known and is typically carried out in a wooden drum (e.g., a hogshead) or cardboard cartons in compressed conditions for several years (e.g., 2 to 5 years), at a moisture content of from about 10% to about 25% (see, for example, U.S. Pat. Nos. 4,516,590 and 5,372,149). Conditioning includes, for example, a heating, sweating or pasteurization step as described in US 2004/0118422 or US 2005/0178398, while fermenting typically is characterized by high initial moisture content, heat generation, and a 10 to 20% loss of dry weight. See, e.g., U.S. Pat. Nos. 4,528,993; 4,660,577; 4,848,373; and 5,372,149. The tobacco also can be further processed (e.g., cut, expanded, blended, milled or comminuted), if desired, and used in a tobacco product.

Tobacco products are known in the art and include any product made or derived from tobacco that is intended for human consumption, including any component, part, or accessory of a tobacco product. Representative tobacco products include, without limitation, cigarettes, smokeless tobacco products, tobacco-derived nicotine products (e.g., tobacco-derived nicotine pieces for use in the mouth), cigarillos, non-ventilated recess filter cigarettes, vented recess filter cigarettes, cigars, snuff, electronic cigarettes, electronic cigars, electronic cigarillos, e-vapor devices, pipe tobacco, cigar tobacco, cigarette tobacco, chewing tobacco, leaf tobacco, shredded tobacco, and cut tobacco. Representative smokeless tobacco products include, for example, chewing tobacco, snus, pouches, films, tablets, sticks, rods, and the like. Representative cigarettes and other smoking articles include, for example, smoking articles that include filter elements or rod elements, where the rod element of a smokeable material can include cured tobacco within a tobacco blend. In addition to the reduced-nicotine or reduced-TSNA tobacco described herein, tobacco products also can include other ingredients such as, without limitation, binders, plasticizers, stabilizers, and/or flavorings. See, for example, US 2005/0244521, US 2006/0191548, US 2012/0024301, US 2012/0031414, and US 2012/0031416 for examples of tobacco products.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Cloning of PR50

Using a subtractive hybridization screening strategy, a differentially expressed PR50, 40S Ribosomal protein S12 homolog is identified from Burley 21 root samples before and 3 days after topping (AF154659.1, Wang et al., 2000, Mol. Biol. Rep., 36:2285-9). A full length PR50 genomic fragment is cloned (SEQ ID NO:1) and sequence comparison shows it to be a single exon gene of 483 nucleotides (SEQ ID NO:2) coding for a putative protein product of 143 amino acids (SEQ ID NO:3).

```
SEQ ID NO: 1:
TGACTAGCTCGTCGTATTGTGGGATGACGATACAT

CACCAGAATCAGTTAGCATGATACGCAGCTGGAAT

ACCTCATCAAGATCAAAAGCTGGAGCTCCCCGCGG

TGGCGGCCGCTCTAGAACTAGTGGATCCCCCGGGC

TGCAGGAATTCGGCACGAGGCATTACTGCAACTCA

AAGCAGATTCGTCGTCTCTAAATTTTAAGGTTGC

TGTGTTTTTTGGGTTTAACATTTACCAAGAAAGA

AATATGTCAGGAGAGGATGCTGCTGTTCCTGTTGT

TGCTGCCGAGACTCCTGCTCCAGCACTTGGGGAGC

CCATGGACATCATGACCGCTCTGCAGCTGGTGCTC

AGGAAGTCTAAAGCTCATGGAGGACTTGCTCGAGG

ACTCCATGAAGGTGCTAAGGTGATTGAGAAGCATG

CTGCGCAGCTTTGTGTGCTAGCAGAGGACTGCGAC

CAGCCAGACTATGTCAAGCTGGTCAAAGCTCTTTG

TGCTGATCACAATGTCAGTTTGATTACAGTTCCCA

ATGCAAAAACTCTTGGCGAATGGGCTGGTTTATGC

AAAATTGATTCTGAAGGGAAAGCAAGGAAAGTTGT

TGGTTGTGGCTGTGTTGTCGTGAAGGATTATGGGG

AAGAGACTGAGGGTCTCCATATCGTCCAGGAGTAC

GTGAAGTCTCATTAAATATAAGGTTGAGATGGAGC

TTTAGGGGACTATGAGGCTAGATAAGTCTGAGACG

GAGCTTTAGGGGGAACTATGAAGCTAGAGATTCC

ATGAGACTATCTTTTTGGCATTTATTTAGAGTTGA

ATTTTTGAGATTTCAAACTATGTTCCCTTATTATT

GTGTTACTTCAAGTTTTGTTTTACCTTCTGGGAAG

ATCTAATAGTTTGAAACTGCCGTCTAGTTTAAAAA

AAAAAAAAAAAAACTCGAGGGGGGGCCCGGTACC

CAATTCTGAGTCGATTACATCCTGCGTCGTTACAC
```

-continued

GTCTGACTGAAACTGCGTACACTATCGCTGAACAT

CCCCTTTCGCACTGGGTAGCGAAAGCTC

SEQ ID NO: 2
ATGTCAGGAGAGGATGCTGCTGTTCCTGTTGTTGC

TGCCGAGACTCCTGCTCCAGCACTTGGGGAGCCCA

TGGACATCATGACCGCTCTGCAGCTGGTGCTCAGG

AAGTCTAAAGCTCATGGAGGACTTGCTCGAGGACT

CCATGAAGGTGCTAAGGTGATTGAGAAGCATGCTG

CGCAGCTTTGTGTGCTAGCAGAGGACTGCGACCAG

CCAGACTATGTCAAGCTGGTCAAAGCTCTTTGTGC

TGATCACAATGTCAGTTTGATTACAGTTCCCAATG

CAAAAACTCTTGGCGAATGGGCTGGTTTATGCAAA

ATTGATTCTGAAGGGAAAGCAAGGAAAGTTGTTGG

TTGTGGCTGTGTTGTCGTGAAGGATTATGGGGAAG

AGACTGAGGGTCTCCATATCGTCCAGGAGTACGTG

AAGTCTCATTAA

SEQ ID NO: 23
ATGTCAGGAGAGGATGCTGCTGTTCCTGTTGTCGC

TGCTGCCGAGACTCCTGCTCCAGCACTTGGGGAGC

CCATGGACATCATGACCGCACTACAGCTGGTGCTA

AAGAAGTCTAAAGCTCATGGAGGACTTGCTCGAGG

ACTCCATGAAGGTGCTAAGGTGATTGAGAAGCATG

CTGCACAGCTTTGTGTGCTAGCTGAGGACTGTGAC

CAGCCAGATTACGTCAAACTGGTGAAAGCACTTTG

TGCTGATCACAATGTCAGTTTAATTACAGTTCCCA

ATGCAAAAACTCTTGGCGAATGGGCTGGTTTATGC

AAAATTGATTCTGAAGGGAAAGCAAGGAAGGTTGT

TGGTTGTGGCTGTGTTGTCGTGAAGGATTATGGTG

AAGAGACTGAGGGTCTCCATATCGTCCAAGAGTAC

GTGAAGTCTCATTA
A

SEQ ID NO: 3
MSGEDAAVPVVAAETPAPALGEPMDIMTALQLVLR

KSKAHGGLARGLHEGAKVIEKHAAQLCVLAEDCDQ

PDYVKLVKALCADHNVSLITVPNAKTLGEWAGLCK

IDSEGKARKVVGCGCVVVKDYGEETEGLHIVQEYV

KSH

SEQ ID NO: 24
MSGEDAAVPVVAAETPAPALGEPMDIMTALQLVL

KKSKAHGGLARGLHEGAKVIEKHAAQLCVLAEDCD

QPDYVKLVKALCADHNVSLITVPNAKTLGEWAGLC

KIDSEGKARKVVGCGCVVVKDYGEETEGLHIVQEY

VKSH

Example 2—RNAi Construct

To study the function of PR50, a RNAi expression vector is constructed and transcribed in tobacco. The pBK-CMV cloning vector is used for the construction of an RNAi vector containing a 502 bp sequence of PR50 in the sense (SEQ ID NO:4) and antisense (SEQ ID NO:5) orientations. These two fragments are separated by a 660 bp Cax-2 spacer (SEQ ID NO:6).

SEQ ID NO: 4
CGAGGCATTACTGCAACTCAAAGCAGATTGCGTCG

TCTCTAAATTTTAAGGTTGCTGTGTTTTTTGGGT

TTAACATTTACCAAGAAAGAAATATGTCAGGAGAG

GATGCTGCTGTTCCTGTTGTTGCTGCCGAGACTCC

TGCTCCAGCACTTGGGGAGCCCATGGACATCATGA

CCGCTCTGCAGCTGGTGCTCAGGAAGTCTAAAGCT

CATGGAGGACTTGCTCGAGGACTCCATGAAGGTGC

TAAGGTGATTGAGAAGCATGCTGCGCAGCTTTGTG

TGCTAGCAGAGGACTGCGACCAGCCAGACTATGTC

AAGCTGGTCAAAGCTCTTTGTGCTGATCACAATGT

CAGTTTGATTACAGTTCCCAATGCAAAAACTCTTG

GCGAATGGGCTGGTTTATGCAAAATTGATTCTGAA

GGGAAAGCAAGGAAAGTTGTTGGTTGTGGCTGTGT

TGTCGTGAAGGATTATGGGGAAGAGACTGAGGGTC

TCCATATCGTCC

SEQ ID NO: 5
GGAGGATATGGAGACCCTGAGTCTCTTCCCCATAA

TCCTTCACGACAACACAGCCACAACCAACAACTTT

CCTTGCTTTCCCTTCAGAATCAATTTTGCATAAAC

CAGCCCATTCGCCAAGAGTTTTTGCATTGGGAACT

GTAATCAAACTGACATTGTGATCAGCACAAAGAGC

TTTGACCAGCTTGACATAGTCTGGCTGGTCGCAGT

CCTCTGCTAGCACACAAAGCTGCGCAGCATGCTTC

TCAATCACCTTAGCACCTTCATGGAGTCCTCGAGC

AAGTCCTCCATGAGCTTTAGACTTCCTGAGCACCA

GCTGCAGAGCGGTCATGATGTCCATGGGCTCCCCA

AGTGCTGGAGCAGGAGTCTCGGCAGCAACAACAGG

AACAGCAGCATCCTCTCCTGACATATTTCTTTCTT

GGTAAATGTTAAACCCAAAAAAACACAGCAACCTT

AAAATTTAGAGACGACGCAATCTGCTTTGAGTTGC

AGTAATGCCTCG

SEQ ID NO: 6
GAATTCGGTGAGTTCCCCCCTCCTCCCCTTTCACT

TTTGTTTGTTGGTTTCTAAGTGCTCTTTCAATTTA

GAGGTTGATGTTGGGAAATAATTAAACAATACTCT

-continued
```
TGTTTTCTAAAATTTCTTGAAAACTACAATGTCTA

TAGAGGCAATATATTTGCTTCTAAACGTTGACGGT

TTTGCAAGTCTTGCGGAGGAGCTTTGATCCAGTGT

TAAAGAAATATATCATGTCTCTTATTCATCCTCCC

TTTCTTTCCTTTGTGTTTTGCTTCACTCCTGGGGT

TTCAACTTTTTCTTTCCGTTTAACCTTTCCTTTT

TTCTGCAGGATGGAACTTCAAATTACTTTAAAGGA

CTGATGCTCCTTCTCTGCTATTGATAGTTGCTGCA

AGTTTCTTTGTGCATATAGATCCAGAGTCTATACG

TAAGTTGTGTTTCTTTTTCGTGAAATTACCATATG

ACATTGACAGCTCCTGGTCTTCGTTTTATTTATTC

TTTTGGTGTTCCTTTTAACCGATAACATCTGTTAT

TATTTCACTGTTACACTAATCTGCTTTGCTTATGG

TGAGTGAGTTTAGCATTAGATTAGATAACGAGTTA

ACCATTTTGGGTCTCGTTAACGTAATATTGTATTG

ATAACTACCTTATCATATATATATCTCTGTTTTAG

TGAATTC
```

The PR50 RNA vector is constructed as follows. The six hundred and sixty bp Cax2 sequence from BAC 57 intron 9 (SEQ ID NO:6) is cloned directly into pBK-CMK at the EcoRI site. XbaI and HindIII sites are added to the 5' and 3' ends of a 502 bp sense-oriented PR50 sequence by means of PCR with primers harboring these restriction enzymes sites (PMG526F: ATT CTA GAC GAG GCA TTA CTG CAA CTC A (SEQ ID NO:7) and PMG 526R: ATA AGC TTG GAC GAT ATG GAG ACC CTC A (SEQ ID NO:8)). Similarly, BamHI and SacI sites are created at the 5' and 3' ends of the corresponding PR50 antisense fragment using PCR with primers harboring these restriction enzyme sites (PMG 527F: ATG AGC TCC GAG GCA TTA CTG CAA CTC A (SEQ ID NO:9) and PMG 527R: ATG GAT TCG GAC GAT ATG GAG ACC CTC A (SEQ ID NO:10)) to produce pBK-CMV-PR50 RNAi plasmid.

To create a plant expression vector capable of mediating the constitutive transcription of PR50 RNAi, the beta-glucuronidase ORF of the binary expression vector, pBI121 (Clontech) is excised and replaced with the 502 bp XbaI-HindIII PR50 sense fragment, the 660 bp Cax2 spacer cloned at the EcoRI site, and the 502 bp BamHI-SacI PR50 antisense fragment by cloning the RNAi nucleic acid molecule into the SbaI/SacI sties of PBI121 to produce a plasmid, PBI121-PR50 RNAi.

Example 3—Transgenic Plants

TN90 cultivar is transformed and select first generation transformants are propagated in the greenhouse. At the flowering stage, plants are topped. Two weeks post-topping, the 3$^{rd}$ and 4$^{th}$ leaf from the top are collected, freeze dried and alkaloids are analyzed using GCMS.

Relative to controls, PR50 RNAi lines show significant reduction in nicotine content (Table 1). Two years of field study of selected transgenic line and a control also show reduced nicotine content (FIG. 3).

TABLE 1

First generation (T0) of transgenic plants showing reduced nicotine

| Plant ID | Nicotine (% by wt) | Nornicotine (% by wt) | Anabasine (% by wt) | Anatabine (% by wt) | Total alkaloids | % nicotine reduction |
|---|---|---|---|---|---|---|
| GH2285 | 0.21 | 0.011 | 0.005 | 0.083 | 0.31 | 90.60 |
| GH2289 | 0.26 | 0.015 | 0.010 | 0.208 | 0.49 | 84.94 |
| GH2261 | 0.41 | 0.021 | 0.007 | 0.174 | 0.61 | 81.12 |
| GH2367 | 0.95 | 0.028 | 0.004 | 0.030 | 1.01 | 69.01 |
| GH2260 | 0.93 | 0.025 | 0.007 | 0.081 | 1.04 | 67.98 |
| GH2368 | 1.20 | 0.031 | 0.006 | 0.046 | 1.28 | 60.55 |
| GH2638 | 1.35 | 0.032 | 0.010 | 0.057 | 1.45 | 55.41 |
| GH2288 | 1.42 | 0.025 | 0.005 | 0.036 | 1.49 | 54.28 |
| GH2280 | 1.54 | 0.029 | 0.005 | 0.042 | 1.62 | 50.27 |
| GH2639 | 1.43 | 0.041 | 0.017 | 0.211 | 1.70 | 47.72 |
| TN90 Control 1 | 2.49 | 0.065 | 0.056 | 0.056 | 2.62 | — |
| TN90 Control 2 | 3.98 | 0.096 | 0.085 | 0.085 | 4.17 | — |

Example 4—Quality of Leaf from Transgenic Plants

Figure 4:
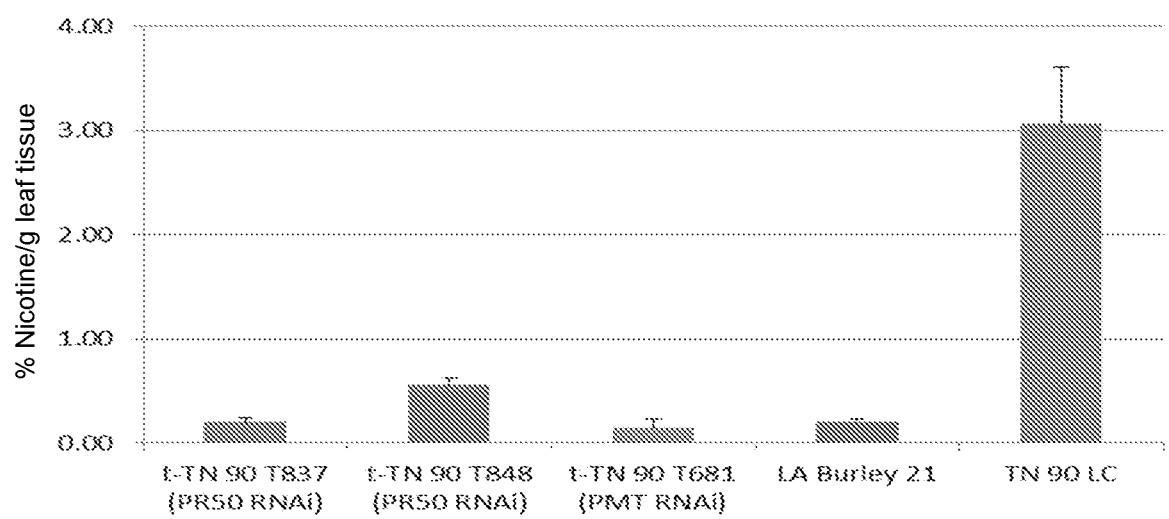
FIG. 4 is a graph showing nicotine levels in TN90 PMT RNAi, TN90 PR50 RNAi, LA Burley 21, and TN90 wild type varieties.

To compare leaf quality in existing low alkaloid tobacco lines with leaf quality in PR50-silenced lines, plants from stable TN90 PR50 RNAi lines along with K326, TN 90, B&W Low Nic, Burley 21 (Heggestad et al., 1960, University of Tennessee Agricultural Experiment Station, Bulletin 321; described therein as having reduced nicotine and nornicotine levels (nic1nic2 genotype)), HI Burley 21 or LI Burley 21 (Nielsen et al., 1988, *Crop Science*, 28:206; described therein as having intermediate levels of total alkaloids), and LA Burley 21 (Legg et al., 1970, *Crop Science*, 10:212; described therein as having "extremely low alkaloid content") were grown in 1 plot rows with 3 replications. All plants were topped at maturity, cured, and leaf samples were collected for evaluation. TN90 PR50 RNAi lines show significantly better leaf quality compared with the other low alkaloid lines. The data from the comparison of nicotine levels in the TN90 PR50 RNAi lines with controls and an in-house low alkaloid line (TN90 PMT RNAi) with respect to leaf quality is shown in FIG. 4.

Example 5—Random Mutagenesis

A novel genetic variation in a population of tobacco plants is created to identify plants for low alkaloids. To induce random mutation, approximately 10,000 seeds of the selected tobacco variety are treated with 0.5% ethyl methane sulfonate (EMS; M1 seed), germinated and propagated (into M1 plants). M2 seeds from self-pollinated M1 plants are collected. A composite of M2 seed is grown and leaves from M2 plants are collected and the DNA extracted. The PR50 sequence is amplified and sequenced, and analyzed for mutations.

Example 6—Targeted Mutagenesis Using TALENs

Transcription activator-like (TAL) effector protein sequences for PR50 are designed (Table 2). The TALs are synthesized and cloned into a plant expression vector (Life Technologies, Inc.) to serve as entry vectors. Depending on the intention, three different protocols are used to generate mutagenic tobacco lines: a) one or more entry vectors containing the target TALs are directly transformed into tobacco protoplasts to generate random sequence deletion or insertion mutagenic tobacco lines; b) a donor sequence (e.g., a reporter gene such as, without limitation, the GUS gene) flanked on the left and right side with sequences that are homologous to the target insertion sequence is co-transformed into tobacco protoplasts with one or more entry vectors to generate mutagenic tobacco lines containing a target sequence interrupted by the donor sequence; or c) a donor sequence containing target TALs containing a point mutation is co-transformed into tobacco protoplasts with one or more entry vectors to generate tobacco lines having a point mutation within the target sequence.

TABLE 2

TALEN Sequences

| TALEN Name | Target Gene | Location | Target Sequence | SEQ ID NO: |
|---|---|---|---|---|
| TALen-PR1 | PR50 | 2-52 | TGTCAGGAGAGGATG CTgctgttcctgttg tt GCTGCCGAGACTCCT GCTCCA | 19 |
| TALen-PR2 | PR50 | 33-101 | TGCTGCCGAGACTCC TGCTCC agcacttggggagcc catggacatcatga CCGCTCTGCAGCTGG TGCTCA | 20 |
| TALen-PR3 | PR50 homologue | 2-55 | TGTCAGGAGAGGATG Ctgctgttcctgttg tcgct GCTGCCGAGACTCCT GCTCCA | 21 |

TABLE 2-continued

TALEN Sequences

| TALEN Name | Target Gene | Location | Target Sequence | SEQ ID NO: |
|---|---|---|---|---|
| TALen-PR4 | PR50 homologue | 126-194 | TGCTGCCGAGACTCC TGCTCC agcacttggggagcc catggacatcatga CCGCTCTGCAGCTGG TGCTCA | 22 |

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of making a tobacco plant, the method comprising:
   (a) inducing mutagenesis in a tobacco cell to produce a mutagenized tobacco cell, wherein the mutagenized tobacco cell comprises a mutation in an endogenous nucleic acid molecule encoding a PR50 polypeptide having the amino acid sequence of SEQ ID NO: 3; and
   (b) obtaining the tobacco plant from the mutagenized tobacco cell, wherein the tobacco plant comprises the mutation, wherein the tobacco plant exhibits a reduced amount of nicotine relative to a corresponding control tobacco plant lacking the mutation, and wherein the tobacco plant exhibits reduced activity of the PR50 polypeptide as compared to a control tobacco plant lacking the mutation.

2. The method of claim 1, wherein the tobacco plant further comprises leaf exhibiting equal or better leaf quality as compared to the control tobacco plant.

3. The method of claim 1, wherein the mutation is selected from the group consisting of an insertion, a deletion, a substitution, and any combination thereof.

4. The method of claim 1, wherein the mutation results in a truncated polypeptide as compared to SEQ ID NO: 3.

5. The method of claim 1, wherein the tobacco plant is selected from the group consisting of a Burley tobacco plant, a dark tobacco plant, a flue-cured tobacco plant, and an Oriental tobacco plant.

6. The method of claim 1, wherein the mutation is a random mutation.

7. The method of claim 1, wherein the mutation is a targeted mutation.

8. The method of claim 1, wherein the mutagenesis is induced via a chemical mutagen or ionizing radiation.

9. The method of claim 8, wherein the chemical mutagen is selected from the group consisting of nitrous acid, sodium azide, acridine orange, ethidium bromide, and ethyl methane sulfonate.

10. The method of claim 8, wherein the ionizing radiation is selected from the group consisting of X-rays, gamma rays, fast neutron radiation, and ultraviolet radiation.

11. A method of making a tobacco plant, the method comprising:
    (a) inducing mutagenesis in a tobacco cell to produce a mutagenized tobacco cell, wherein the mutagenized tobacco cell comprises a mutation in an endogenous nucleic acid molecule encoding a PR50 polypeptide having the amino acid sequence of SEQ ID NO: 3;
    (b) obtaining the tobacco plant from the mutagenized tobacco cell, wherein the tobacco plant comprises the mutation; and (c) self-pollinating the tobacco plant obtained in step (b) to produce a progeny tobacco plant comprising the mutation, wherein the progeny tobacco plant exhibits a reduced amount of nicotine relative to a corresponding control tobacco plant lacking the mutation, and wherein the progeny tobacco plant exhibits reduced activity of the PR50 polypeptide as compared to a control tobacco plant lacking the mutation.

12. The method of claim 11, wherein the tobacco plant further comprises leaf exhibiting equal or better leaf quality as compared to the control tobacco plant.

13. The method of claim 11, wherein the mutation is selected from the group consisting of an insertion, a deletion, a substitution, and any combination thereof.

14. The method of claim 11, wherein the mutation results in a truncated polypeptide as compared to SEQ ID NO: 3.

15. The method of claim 11, wherein the tobacco plant is selected from the group consisting of a Burley tobacco plant, a dark tobacco plant, a flue-cured tobacco plant, and an Oriental tobacco plant.

16. The method of claim 11, wherein the mutation is a random mutation.

17. The method of claim 11, wherein the mutation is a targeted mutation.

18. The method of claim 11, wherein the mutagenesis is induced via a chemical mutagen or ionizing radiation.

19. The method of claim 18, wherein the chemical mutagen is selected from the group consisting of nitrous acid, sodium azide, acridine orange, ethidium bromide, and ethyl methane sulfonate.

20. The method of claim 18, wherein the ionizing radiation is selected from the group consisting of X-rays, gamma rays, fast neutron radiation, and ultraviolet radiation.

\* \* \* \* \*